(12) United States Patent
Harai et al.

(10) Patent No.: US 7,226,408 B2
(45) Date of Patent: Jun. 5, 2007

(54) TACK DEVICE WITH SHIELD

(75) Inventors: Boaz Harai, Haifa (IL); Mordechay Beyar, Caesarea (IL); Oren Globerman, Kfar-Shmaryahu (IL)

(73) Assignee: AMS Research Corporation, Minnetonka, MN (US)

( * ) Notice: Subject to any disclaimer, the term of this patent is extended or adjusted under 35 U.S.C. 154(b) by 714 days.

(21) Appl. No.: 10/322,891

(22) Filed: Dec. 18, 2002

(65) Prior Publication Data

US 2003/0135225 A1    Jul. 17, 2003

Related U.S. Application Data

(60) Division of application No. 09/684,108, filed on Oct. 6, 2000, now Pat. No. 6,544,273, which is a continuation-in-part of application No. 09/475,870, filed on Dec. 30, 1999, now Pat. No. 6,387,041.

(30) Foreign Application Priority Data

Jan. 8, 1999    (IL) .................................. 127978

(51) Int. Cl.
*A61F 13/00* (2006.01)
*A61B 17/00* (2006.01)
(52) U.S. Cl. ................ 600/37; 606/1; 606/151
(58) Field of Classification Search ............ 606/1, 606/104, 151; 600/37
See application file for complete search history.

(56) References Cited

U.S. PATENT DOCUMENTS

| | | |
|---|---|---|
| 2,738,790 A | 3/1956 | Todt et al. |
| 3,580,313 A | 5/1971 | McKnight |
| 3,995,619 A | 12/1976 | Glatzer |
| 4,172,458 A | 10/1979 | Pereyra |
| 4,632,100 A | 12/1986 | Somers et al. |
| 4,873,976 A | 10/1989 | Schreiber |
| 4,920,986 A | 5/1990 | Biswas |
| 5,007,894 A | 4/1991 | Enhorning |
| 5,012,822 A | 5/1991 | Schwarz |
| 5,013,316 A | 5/1991 | Goble et al. |
| 5,019,032 A | 5/1991 | Robertson |
| 5,036,867 A | 8/1991 | Biswas |

(Continued)

FOREIGN PATENT DOCUMENTS

DE    2305815    2/1973

(Continued)

OTHER PUBLICATIONS

Beck, Peter R. et al., Treatment of Urinary Stress Incontinence With Anterior Colporrhaphy, Obstetrics and Gynecology, vol. 59 (No. 3), pp. 269-274 (Mar. 1982).

(Continued)

*Primary Examiner*—Gary Jackson
(74) *Attorney, Agent, or Firm*—Barbara A. Wrigley; Oppenheimer Wolff & Donnelly LLP; José W. Jimenez

(57) ABSTRACT

A slotted shield for a surgical tack, including a body adapted to engage a tack head. The shield has at least one slot having a width, defined by the body. Optionally, the shield is mounted on a tack head on which said shield is mounted.

8 Claims, 18 Drawing Sheets

U.S. PATENT DOCUMENTS

| | | | |
|---|---|---|---|
| 5,085,661 A | 2/1992 | Moss | |
| 5,123,428 A | 6/1992 | Schwarz | |
| 5,188,636 A | 2/1993 | Fedotov | |
| 5,209,756 A | 5/1993 | Seedhom et al. | |
| 5,256,133 A | 10/1993 | Spitz | |
| 5,281,237 A | 1/1994 | Gimpelson | |
| 5,328,077 A | 7/1994 | Lou | |
| 5,362,294 A | 11/1994 | Seitzinger | |
| 5,376,097 A | 12/1994 | Phillips | |
| 5,386,836 A | 2/1995 | Biswas | |
| 5,413,598 A | 5/1995 | Moreland | |
| 5,439,467 A | 8/1995 | Benderev et al. | |
| 5,520,700 A | 5/1996 | Beyar et al. | |
| 5,527,342 A | 6/1996 | Pietrzak et al. | |
| 5,544,664 A | 8/1996 | Benderev et al. | |
| 5,562,689 A | 10/1996 | Green et al. | |
| 5,571,139 A | 11/1996 | Jenkins, Jr. | |
| 5,582,188 A | 12/1996 | Benderev et al. | |
| 5,584,860 A * | 12/1996 | Goble et al. | 606/232 |
| 5,611,515 A | 3/1997 | Benderev et al. | |
| 5,643,320 A | 7/1997 | Lower et al. | |
| 5,674,247 A | 10/1997 | Sohn et al. | |
| 5,683,349 A | 11/1997 | Makower et al. | |
| 5,697,931 A | 12/1997 | Thompson | |
| 5,709,708 A | 1/1998 | Thal | |
| 5,725,541 A | 3/1998 | Anspach, III et al. | |
| 5,741,282 A | 4/1998 | Anspach, III et al. | |
| 5,782,862 A * | 7/1998 | Bonutti | 606/232 |
| 5,807,403 A | 9/1998 | Beyar et al. | |
| 5,836,314 A | 11/1998 | Benderev et al. | |
| 5,836,315 A | 11/1998 | Benderev et al. | |
| 5,842,478 A | 12/1998 | Benderev et al. | |
| 5,860,425 A | 1/1999 | Benderev et al. | |
| 5,873,891 A | 2/1999 | Sohn | |
| 5,899,909 A | 5/1999 | Claren et al. | |
| 5,922,026 A | 7/1999 | Chin | |
| 5,925,047 A | 7/1999 | Errico et al. | |
| 5,944,732 A | 8/1999 | Raulerson et al. | |
| 5,972,000 A | 10/1999 | Beyar et al. | |
| 5,980,558 A | 11/1999 | Wiley | |
| 5,984,927 A | 11/1999 | Wenstrom, Jr. et al. | |
| 5,988,171 A | 11/1999 | Sohn et al. | |
| 5,997,554 A | 12/1999 | Thompson | |
| 6,007,539 A | 12/1999 | Kirsch et al. | |
| 6,010,447 A | 1/2000 | Kardjian | |
| 6,019,768 A * | 2/2000 | Wenstrom et al. | 606/104 |
| 6,027,523 A | 2/2000 | Schmieding | |
| 6,030,393 A | 2/2000 | Corlew | |
| 6,036,701 A | 3/2000 | Rosenman | |
| 6,039,686 A | 3/2000 | Kovac | |
| 6,042,534 A | 3/2000 | Gellman et al. | |
| 6,042,536 A | 3/2000 | Tihon et al. | |
| 6,042,583 A | 3/2000 | Thompson et al. | |
| 6,048,351 A | 4/2000 | Gordon et al. | |
| 6,053,935 A | 4/2000 | Brenneman et al. | |
| 6,056,688 A | 5/2000 | Benderev et al. | |
| 6,068,591 A | 5/2000 | Bruckner et al. | |
| 6,077,216 A | 6/2000 | Benderev et al. | |
| 6,099,551 A | 8/2000 | Gabbay | |
| 6,099,552 A | 8/2000 | Adams | |
| 6,200,330 B1 | 3/2001 | Benderev et al. | |
| 6,241,736 B1 | 6/2001 | Sater et al. | |
| 6,245,082 B1 | 6/2001 | Gellman et al. | |
| 6,264,676 B1 | 7/2001 | Gellman et al. | |
| 6,319,272 B1 | 11/2001 | Brenneman | |
| 6,322,492 B1 | 11/2001 | Kovac | |
| 6,328,686 B1 | 12/2001 | Kovac | |
| 6,328,744 B1 | 12/2001 | Harari et al. | |
| 6,334,446 B1 | 1/2002 | Beyar | |
| 6,382,214 B1 | 5/2002 | Raz et al. | |
| 6,387,041 B1 | 5/2002 | Harari et al. | |
| 6,406,480 B1 * | 6/2002 | Beyar et al. | 606/104 |
| 6,423,072 B1 | 7/2002 | Zappala | |
| 6,440,154 B2 | 8/2002 | Gellman et al. | |
| 6,454,778 B2 | 9/2002 | Kortenbach | |
| 6,544,273 B1 * | 4/2003 | Harari et al. | 606/151 |
| 2001/0000533 A1 | 4/2001 | Kovac | |
| 2001/0027321 A1 | 10/2001 | Gellman et al. | |
| 2001/0041895 A1 | 11/2001 | Beyar et al. | |
| 2002/0022841 A1 | 2/2002 | Kovac | |
| 2002/0035369 A1 | 3/2002 | Beyar et al. | |
| 2002/0038119 A1 | 3/2002 | Weber et al. | |
| 2002/0038132 A1 | 3/2002 | Abrams | |
| 2002/0050277 A1 | 5/2002 | Beyar | |
| 2002/0095064 A1 | 7/2002 | Beyar | |
| 2002/0095163 A1 | 7/2002 | Beyar | |
| 2002/0095181 A1 | 7/2002 | Beyar | |
| 2002/0128681 A1 | 9/2002 | Broome et al. | |

FOREIGN PATENT DOCUMENTS

| | | |
|---|---|---|
| RU | 1225547 | 4/1986 |
| WO | WO 93/19678 A2 | 10/1993 |
| WO | WO 95/11631 A1 | 5/1995 |
| WO | WO 95/25469 A1 | 9/1995 |
| WO | WO 97/47244 A2 | 12/1997 |
| WO | WO 98/19606 A1 | 5/1998 |
| WO | WO 98/35606 A2 | 8/1998 |
| WO | WO 98/35632 A2 | 8/1998 |
| WO | WO 98/42261 A1 | 10/1998 |
| WO | WO 98/53746 A1 | 12/1998 |
| WO | WO 99/37216 A1 | 7/1999 |
| WO | WO 99/37217 A1 | 7/1999 |
| WO | WO 99/53829 A1 | 10/1999 |
| WO | WO 99/53844 A1 | 10/1999 |
| WO | WO 99/58074 A2 | 11/1999 |
| WO | WO 0040158 A2 | 7/2000 |

OTHER PUBLICATIONS

Benderev, Theodore V., MD, A Modified Percutaneous Outpatient Bladder Neck Suspension System, Journal of Urology, vol. 152, pp. 2316-2320 (Dec. 1994).

Benderev, Theodore V., MD, Anchor Fixation and Other Modifications of Endoscopic Bladder Neck Suspension, Urology, vol. 40, No. 5, pp. 409-418 (Nov. 1992).

Blaivis, J. G. et al., Pubovaginal Fascial Sling for the Treatment of Complicated Stress Urinary Incontinence, J. Urology 145(6): 1214-18 (Jun. 1991).

Brochure, Vesica Percutaneous Bladder Neck Stabilization Kit, Microvasive Boston Scientific Corporation (1995).

Burch, John C., Urethrovaginal Fixation to Cooper's Ligament for Correction of Stress Incontinence, Cystocele, and Prolapse, Am. Journal Obstetrics & Gynecology, vol. 81 (No. 2), pp. 281-290 (Feb. 1961).

Das, Saki et al., Laparoscopic Colpo-Suspension, The Journal of Urology, vol. 154, pp. 1119-1121 (Sep. 1995).

Gilja, Ivan et al., A Modified Raz Bladder Neck Suspension Operation (Transvaginal Burch), The Journal of Urology, vol. 153, pp. 1455-1457 (May 1995).

Gittes, Ruben F. et al., No-Incision Pubovaginal Suspension for Stress Incontinence, The Journal of Urology, vol. 138, pp. 568-570(Sep. 1987).

Holschneider, C. H., et al., The Modified Pereyra Procedure in Recurrent Stress Urinary Incontinence: A 15-year Review, Obstetrics & Gynecology, vol. 83, No. 4, pp. 573-578 (Apr. 1994).

Horbach, Nicollette S., et al., Instruments and Methods, A Suburethral Sling Procedure with Polytetrafluoroehtylene for the Treatment of Genuine Stress Incontinence in Patients with Low Urethral Closure Pressure, Obstetrics & Gynecology, vol. 71, No. 4, pp. 648-652 (Apr. 1998).

Klutke, John James et al., The Anatomy of Stress Incontinence: Magnetic Resonance Imaging of the Female Bladder Neck and Urethra, The Journal of Urology, vol. 143, pp. 563-566 (Mar. 1990).

Klutke, John James et al., Transvaginal Bladder Neck Suspension to Cooper's Ligament: A Modified Pereyra Procedure, Obstetrics & Gynecology, vol. 88, No. 2, pp. 294-296 (Aug. 1996).

Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).

Leach, Gary E., MD, Bone Fixation Technique for Transvaginal Needle Suspension, Urology vol. XXXI, No. 5, pp. 388-390 (May 1988).

Leach, Gary E., MD, et al., Female Stress Urinary Incontinence Clinical Guidelines Panel Summary D171Report on Surgical Management of Female Stress Urinary Incontinence, American Urological Association, vol. 158, pp. 875-880, (Sep. 1997).

Loughlin, Kevin R. et al., Review of An 8-Year Experience with Modifications of Endoscopic Suspension of the Bladder Neck for Female Stress Incontinence, The Journal of Urology, vol. 143, pp. 44-45 (Jan. 1990).

Marshall, Victor Fray et al., The Correction of Stress Incontinence by Simple Vesicourethral Suspension, Surgery, Gynecology and Obstetrics, vol. 88, pp. 509-518 (May 1949).

Mascio, Valenzio C., MD, Therapy of Urinary Stress Incontinence in Women Using Mitek GII Anchors, Mitek Brochure "GI Anchor System" 5 pages (Apr. 1993).

McGuire, E. J. et al., Pubovaginal Sling Procedure for Stress Incontinence, J. Urol. 119(1): 82-4 (Jan. 1978).

McGuire, E.J., Abdominal Procedure for Stress Incontinence, Urol. Clin. North Am., 12(2): 285-90 (May 1985).

McGuire, Edware J., MD, The Sling Procedure for Urinary Stress Incontinence, Profiles in Urology, pp. 2-18, no date.

McKiel, Charles F., Jr. et al., Marshall-Marchetti Procedure Modification, The Journal of Urology, vol. 96, pp. 737-739 (Nov. 1966).

Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).

Parra, R. O. et al., Experience with a Simplified Technique for the Treatment of Female Stress Urinary Incontinence, British Journal of Urology, vol. 66, pp. 615-617 (1990).

Pereyra, Armand J. et al., Pubourethral Supports in Perspective: Modified Pereyra Procedure for Urinary Incontinence, Obstetrics and Gynecology, vol. 59, No. 5, pp. 643-648 (May 1982).

Precision Tack™ Transvaginal Anchor System, Boston Scientific Microvasive®, 4 pages (1998).

Precision Tack™ Transvaginal Anchor System, Boston Scientific Microvasive®, 2 pages (2000).

Raz, Shlomo, et al., The Raz Bladder Neck Suspension Results in 206 Patients, The Journal of Urology, pp. 845-846 (1992).

Raz, Shlomo, MD, Modified Bladder Neck Suspension for Female Stress Incontinence, Urology, vol. XVII, No. 1, pp. 82-85 (Jan. 1981).

Sling (advertisement), Vesica Sling Kit, Microvasive Boston Scientific Corporation, 1 page, no date.

Spencer, Julia R. et al., A Comparison of Endoscopic Suspension of the Vesical Neck with Suprapubic Vesicourethropexy for Treatment of Stress Urinary Incontinence, The Journal of Urology, vol. 137, pp. 441-415 (Mar. 1987).

Stamey, Thomas A., MD, Endoscopic Suspension of the Vesical Neck for urinary Incontinence, Surgery, Gynecology & Obstetrics, vol. 136, pp. 547-554 (Apr. 1973).

Ulmsten, U. et al., An-Ambulatory Surgical Procedure Under Local Anesthesia for Treatment of Female Urinary Incontinence, International Urogynecology Journal, vol. 7, pp. 81-86 (May 1996).

Waxman, Steve et al., Advanced Urologic Surgery for Urinary Incontinence, The Female Patient, vol. 21, pp. 93-100 (Mar. 1996).

Webster, George D., Female Urinary Incontinence, Urology, pp. 665-679, no date.

Winter, Chester C., Peripubic Urethropexy for Urinary Stress Incontinence in Women, Urology, vol. XX, No. 4, pp. 408-411 (Oct. 1982).

Zimmern, Phillippe E. et al., Four-Corner Bladder Neck Suspension, Vaginal Surgery for the Urologist, vol. 2, No. 1, pp. 29-36 (Apr. 1994).

* cited by examiner

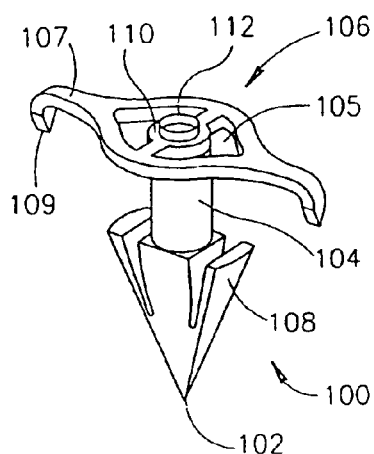
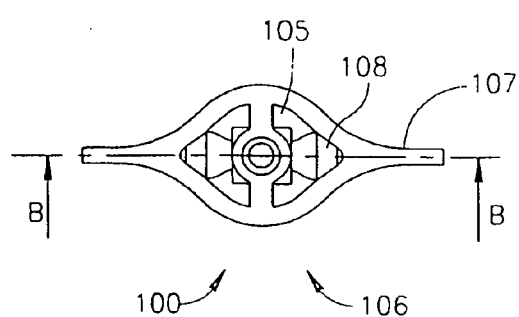
FIG.9A　　　　　　　　FIG.9B
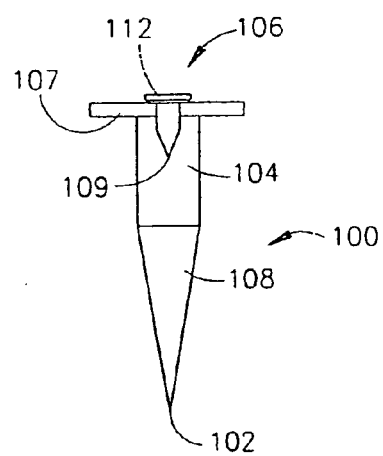
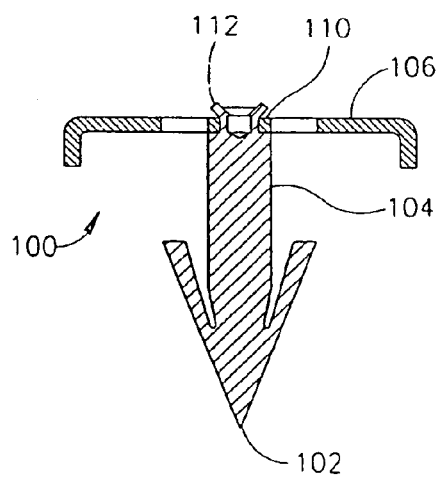
FIG.9C　　　　　　　　FIG.9D

TACK DEVICE WITH SHIELD

RELATED APPLICATIONS

This application is a Divisional of U.S. patent application Ser. No. 09/684,108, filed Oct. 6, 2000 U.S. Pat. No. 6,544,273, which was a Continuation-In-Part (CIP) of U.S. patent application Ser. No. 09/475,870, filed Dec. 30, 1999, issued on May 14, 2002 as U.S. Pat. No. 6,387,041 which claims priority to Israeli patent application serial number 127978, filed Jan. 8, 1999, the disclosures of which are incorporated herein by reference.

FIELD OF THE INVENTION

The present invention relates to methods and apparatus for treating incontinence, especially by bladder neck support.

BACKGROUND OF THE INVENTION

Urinary incontinence is an unfortunately common medical complaint. Many treatments have been suggested. Recently, a relatively minimally invasive technique has become more common, in which a bladder neck and/or urethra is supported by a sling, so that the urethra is partially compressed and/or has a support below it so that during straining and/or bladder/uretheral descent, pressure is applied between the urethra and the sling, thereby closing its lumen.

Benderev et. al, in U.S. Pat. No. 5,836,314 and Brenneman et al, in PCT publication WO 98/19606, the disclosures of which are incorporated herein by reference, describe exemplary procedures for treating incontinence. Two or more bone anchors are attached to the pubic bone. Each anchor is pre-threaded with a suture. Brenneman suggests attaching a sling to the sutures such that when the sutures are pulled tight and knotted, the sling is urged towards the pubic bone. Benderev suggests integrally molding one end of a suture with a "suture support," which suture support is provided to prevent damage to the urethra by the sutures.

It should be noted that, prior to the introduction of slings, some earlier procedures, for example the Burch procedure and the M.M.K. procedure, used only sutures without a sling to support the bladder neck. Also the, different, needle bladder neck suspension procedure uses only sutures. The disadvantage of these procedures is that the bare sutures can cut into and damage the urethra. In a sling procedure, described below, a mesh or a wide strip of material contacts the urethra instead of sutures, so that the urethra is not damaged.

FIG. 1 is a schematic side cut-through illustration of a pubic region 20 during such a procedure, before the sutures are tightened. In the figure, a sling 32 is located between a vagina 22 and a bladder neck 26 of a bladder 24. The sling is threaded by a plurality of sutures 36, which are attached to a bone anchor 30, in a pubic bone 28.

There are two commonly applied methods of bringing sling 32 to a position between vagina 22 and bladder neck 26. In a first method, an incision is made in the vagina, at an area corresponding to that marked with reference number 34, perpendicular to the figure plane, thereby forming a flap. The sling is inserted into the incision, under the flap, and after the sling is tightened, the incision is closed. In a second method, only a small hole in the vagina lining is made for each inserted bone anchor and a tunnel is formed between the two holes, for insertion of sling 32 therethrough.

This family of suture-sling techniques has several disadvantages:

(a) the suture is an additional element which may be damaged during the procedure or after it;

(b) knotting the sutures (after they are tightened) takes skill and time; additionally, some patients have complained that the sutures cause discomfort during sexual activity, since such sutures typically have sharp edges and are often bulky as the suture may have to be knotted as many as six times to assure patency;

(c) the sutures add some unwanted leeway between the positioning of the anchors and the positioning of the ends of the sling; and (d) the sutures may damage the sling by cutting through it (older tissue being more susceptible); if the suture enters the sling at multiple points (to reduce strain at the sling-suture joints) the sling may be deformed by the sutures.

U.S. Pat. No. 3,580,313, to McKnight, the disclosure of which is incorporated herein by reference, suggests using the tissue between the urethra and the vagina as a "sling" and stapling that tissue to the pubic bone. However, this solution may not be suitable for some patients, such as older patients, as their tissue are usually too weak to provide a suitable support. Also, older tissue is more susceptible to cut-through damage from the staples.

SUMMARY OF THE INVENTION

An aspect of some preferred embodiments of the present invention relates to a sutureless method of supporting a bladder neck. In a preferred embodiment of the invention, the bladder neck is supported by a sling, and the sling is directly tacked to a pubic bone, without intermediate sutures. Alternatively or additionally, the sling is directly attached to the bone using other means, for example an adhesive. As used herein "directly attached" means attached without an intermediate suture. In many cases, the sling will not be in direct physical contact with the bone. Generally, but not necessarily, there will be only tissue (if any) between the sling and the bone. However, in a preferred embodiment of the invention, there will not be a suture or other implant between the sling and the bone.

It is noted that by not requiring sutures, the previously required step of tightening and tying the sutures is not required.

An aspect of some embodiments of the invention relates to a tack shield. In an exemplary embodiment of the invention, when a tack is mounted on a tack head, for use in the body, the tack is surrounded by a shield, so that the tack tip and/or other parts of the tack, do not inadvertently damage the body. In an exemplary embodiment of the invention, the shield is retractable. Alternatively or additionally, the shield is flexible or bendable, being pushed back by forceful contact of the shield with a bone, to reveal the tack.

In an exemplary embodiment of the invention, the shield includes at least one slot adapted for receiving a sling from the side of the shield. Thus, the sling can lie flat while it is mounted on the tack and the shield is protecting the body from the tack. Optionally, the shield is rotationally fixed relative to the tack head, so that the sling placement can be known outside the body.

The entire shield need not be flexible, for example, only the part defining the slot(s) may be flexible. However, it may be simpler to manufacture the shield from a single material.

An aspect of some embodiments of the invention relates to a device for assisting in mounting a sling on a tack. In an exemplary embodiment of the invention, the device comprises a peg portion with an aperture formed at a tip thereof, for reversibly receiving the tip of a tack. In operation, a sling is placed between the aperture and the tack tip, and the peg is advanced towards the tack, forcing the tack tip to penetrate the sling. Optionally, the peg includes a finger guard, to protect fingers holding the peg from the tip of the tack, if the peg slips. Alternatively, a peg-like tip may be mounted on a handle, for example a perpendicular bar. Alternatively or additionally, a portion of the peg, near the aperture is slightly tacky, to engage the sling prior to mounting. Alternatively or additionally, the peg near the aperture is slotted, to hold the sling. In an exemplary embodiment of the invention, the peg diameter is larger than the sling width.

In an exemplary embodiment of the invention, the sling mounting device is used in conjunction with a slotted shield. Alternatively or additionally, the sling mounting device can apply enough force to bend back the shield. Optionally, the peg portion is mounted on one jaw of a pliers, with the other jaw adapted to engage the tack head behind the tack, for example, so that a greater contact force can be applied and/or so that the tack head does not inadvertently move.

Alternatively to the aperture reversibly receiving the tack tip, in an exemplary embodiment of the invention, the peg is a one-time device. In one example, the peg must be broken in order to remove it from the tip. Optionally, the peg includes a draw string down its side for splitting the peg.

An aspect of some preferred embodiments of the invention relates to a sling that is preloaded with one or more tacks at one or both ends thereof prior to insertion into a body. In a preferred embodiment of the invention, the pre-loaded sling is mounted on a tacker, for insertion into the body. Alternatively, the sling is not provided as pre-mounted on a tack and is mounted on a tack only after the tack is mounted on a tacker with a protruding tack. Optionally, the mounting of the sling is a two step process, in which the tack is assembled after the sling is mounted on it.

An aspect of some preferred embodiments of the invention relates to tacks with wide heads. In a preferred embodiment of the invention, a tack comprises a shaft and a head, where the head has a maximum extent perpendicular to the shaft, which extent (the width of the head) is considerably greater the shaft diameter. Alternatively or additionally, the width of the head is made considerably greater than a maximum extent of a bone-entering portion of the tack (which is usually wider than the shaft). Thus, the head is larger than the hole formed in the sling by its being tacked and the head can maintain the sling in place. In a preferred embodiment of the invention, the head is substantially circular or polygonal. Alternatively, the head is a bar-shaped beam which is perpendicular to the shaft. As used herein "considerably larger" means 50%, 100%, 200%, 400% larger or more. Although the head may be large, it is not necessarily solid. Rather, one or more holes may be formed in the head. Optionally, these holes are used for threading the sling through them.

In some preferred embodiments of the invention the head can rotate relative to the shaft.

An aspect of some preferred embodiments of the invention relates to disassembled or deformable tacks, in which a sling may be pierced with a small diameter portion of the tack. The tack is then assembled or deformed, so that the head and/or bone entering portions of the tack have a larger diameter than the piercing portion. In one example, the tack comprises two parts, a head with a shaft portion and a bone-entering portion. The sling is pierced by the shaft portion and then the bone-entering portion is attached to a protruding end of the tack. In another embodiment, the bone-entering portion is maintained at a small diameter until after it pierces the sling, for example by a fin in the shaft receding into a recess formed in the shaft or by the shaft being expandable. In another example, the head is separate from the shaft.

An aspect of some preferred embodiments of the invention relates to an attachment to a bone stapler, which attachment holds a sling in place over a staple-exit portion of the stapler, to enable a standard stapler or a standard bone-anchor inserter to be used for tacking slings in accordance with a preferred embodiment of the invention. In a preferred embodiment of the invention, the type of stapler provided is such that the tip of the staple does not protrude from the stapler, so the sling is preferably maintained in place solely by the attachment. In an alternative embodiment, the tip of the staple does protrude from the stapler and may serve to at least partially hold the sling, while the attachment fixes the orientation of the sling relative to the staple or the attachment. If a two prong staple (or tack) is used, such an attachment may serve solely to keep the sling from slipping off the tip of the staple.

An aspect, of some preferred embodiments of the invention, relates to a tacker which includes two stapling heads, for simultaneous tacking of two sides of a sling. In a preferred embodiment of the invention, the tacker comprises two arms, with a tacking head at the end of each arm. Preferably the angle between the arms is controllable to adapt the tacker for different length slings. In a preferred embodiment of the invention, the sling is pre-mounted on the two heads prior to insertion into the body.

There is thus provided in accordance with a preferred embodiment of the invention, a surgical tack, comprising:
  a single shaft formed of a bio-compatible material and having a tip adapted for entering and engaging bone; and
  a head mounted on said shaft, said head adapted for engaging a substrate between said head and said bone. Preferably, said shaft is a separate element from said head. Preferably, said head is rotatable relative to said shaft. Alternatively or additionally, said head is mounted in a slot defined at an end of said shaft. Alternatively or additionally, said head is mounted on a narrowing of said shaft.

In a preferred embodiment of the invention, said head comprises only one arm extending substantially perpendicular to said shaft.

In a preferred embodiment of the invention, said head comprises at least two arms extending substantially perpendicular to said shaft. Alternatively, said head comprises at least one arm extending at an angle to said shaft.

In a preferred embodiment of the invention, said head defines a plurality of apertures therethrough. Alternatively or additionally, said head comprises a plurality of protrusions extending in a direction of said tip, which protrusions are adapted for engaging said substrate. Preferably, said protrusions are smooth at a portion thereof where they engage said substrate. Alternatively, said protrusions are pointed at a portion thereof where they engage said substrate.

In a preferred embodiment of the invention, said protrusions extend at least half a thickness of the substrate.

In a preferred embodiment of the invention, the tack comprises at least one fin extending from said shaft, distal from said head, and adapted for engaging said bone after insertion of said shaft into said bone. Preferably, said at least one fin comprises at least two angularly spaced apart fins. Alternatively or additionally, said at least one fin comprises at least two axially spaced apart fins. Alternatively or additionally, said at least one fin comprises a separate element from said shaft. Alternatively, said at least one fin is integrally formed with said shaft.

In a preferred embodiment of the invention, said shaft defines a recess and said at least one fin is adapted for recessing into said defined recess, when force having a vector perpendicular to said shaft is applied to said fin.

In a preferred embodiment of the invention, said at least one fin is mounted on a separate fin element, which is attached to said shaft.

In a preferred embodiment of the invention, said head is roughened at a portion thereof that engages said substrate.

In a preferred embodiment of the invention, said tack comprises an advance-stop on said shaft adjacent said head and separate from said head, such that said advance-stop prevents said head, at portions near said shaft, from touching said bone. Alternatively or additionally, said head has two configurations, one in which it has an substantially large transaxial extent and one in which it has a substantially small transaxial extent.

There is also provided in accordance with a preferred embodiment of the invention, a tack insertion device, comprising:

a "C" shaped body;

a handle at one end of said body;

a slotted tack holder at a second end of said body, wherein said slotted tack holder holds a tack pointed towards said handle and wherein said slot is adapted for frictionally engaging a tack.

Preferably, said slotted head is adapted to engage a tack having a multi-arm head. Alternatively or additionally, said slotted head is adapted to engage a tack having an apertured head.

In a preferred embodiment of the invention, said device comprises a second tack holder attached to said body at an offset from said first tack holder. Preferably, said device comprises a selectable offsetting mechanism for setting said offset.

In a preferred embodiment of the invention, said device comprises a safety release mechanism that prevents the release of said tack.

There is also provided in accordance with a preferred embodiment of the invention, a method of preparing a sling combination, comprising:

providing a sling formed of a biocompatible material and having two ends;

mounting said sling on a first tack at a first end of the sling; and mounting said first tack on a tacking device. Preferably, said method comprises mounting said sling on a second tack at a second end of said sling. Preferably, said method comprises mounting said second tack on said tacking device.

In a preferred embodiment of the invention, said method comprises adjusting an offset between two tacking heads of said tacking device.

In a preferred embodiment of the invention, said method comprises cutting said sling to said after mounting said first tack on said sling.

In a preferred embodiment of the invention, mounting said sling on said first tack is performed after said tack is mounted on said tacking device. Alternatively, mounting said sling on said first tack is performed before said tack is mounted on said tacking device.

In a preferred embodiment of the invention, the method comprises assembling said first tack after mounting said sling on said first tack. Alternatively, the method comprises assembling said first tack after mounting said first tack on said tacking device.

Preferably, assembling said first tack comprises attaching a head to a shaft of said tack. Alternatively or additionally, assembling said first tack comprises attaching at least one fin to a shaft of said tack.

In a preferred embodiment of the invention, mounting said sling on said tack comprises piercing said sling by said tack. Alternatively, mounting said sling on said tack comprises inserting said tack into a hole in said sling.

In a preferred embodiment of the invention, the method comprises inserting at least a part of said tacking device into a human vagina, after mounting said tack on the tacking device.

There is also provided in accordance with a preferred embodiment of the invention, a kit, comprising:

a sling having a length suitable for bladder neck supporting; and at least one tack, having a head and a shaft, wherein said head has an extent perpendicular to the shaft, which extent is substantially greater than a diameter of the shaft. Preferably, said sling contains at least one pre-punched aperture. Alternatively or additionally, said sling contains at least two adjacent pre-punched apertures, for setting an effective sling size.

In a preferred embodiment of the invention, said at least one tack comprises at least two tacks. Alternatively or additionally, said sling is reinforced at least at its ends.

There is also provided in accordance with a preferred embodiment of the invention, a kit, comprising:

a sling formed of bio-compatible material and having a length and mechanical properties suitable for bladder neck supporting; and a clip adapted to hold said sling against a tacking head of at least a particular tacking or stapling device.

[new claim synopsis]

BRIEF DESCRIPTION OF THE DRAWINGS

The present invention will be more clearly understood from the following detailed description of the preferred embodiments of the invention and from the attached drawings, in which:

FIGS. 9A-9D illustrate an alternative tack, in accordance with a preferred embodiment of the invention;

DETAILED DESCRIPTION OF THE PREFERRED EMBODIMENTS

Figure 2:
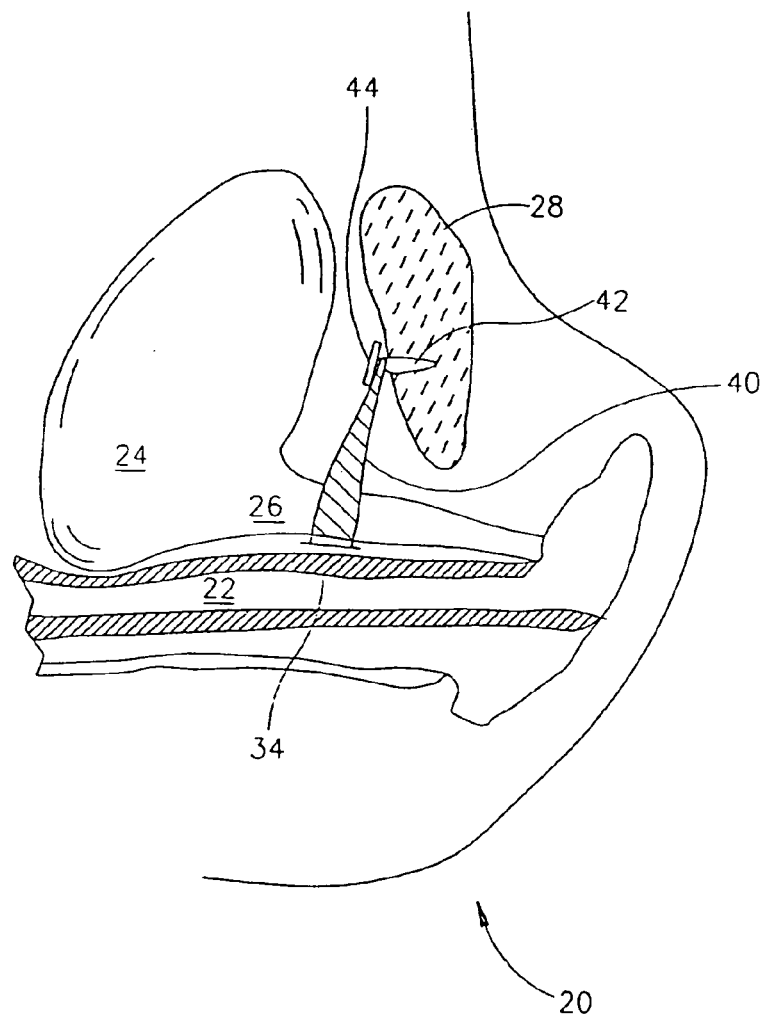
FIG. 2 is a schematic cut-through illustration of a pubic area during a bladder neck support operation, in accordance with a preferred embodiment of the invention.

FIG. 2 is a schematic cut-through illustration of a pubic area during a bladder neck support operation, in accordance with a preferred embodiment of the invention. A sling 40 is shown as being tacked directly to pubic bone 28, by a tack 42 and being held in place by a head 44 of tack 42. In a preferred embodiment of the invention, a shaft of tack 42 pierces sling 40. Alternatively or additionally, the sling is held against the bone by friction, caused by head 44 urging sling 40 against pubic bone 28 (possibly through intervening tissue).

In a preferred embodiment of the invention, the following method is used to attach the sling to the bone:

(a) a first tack is tacked (preferably through sling 40) into a first location on pubic bone 28;

(b) the sling is inserted between vagina 22 and bladder neck 26 or the urethra: access is preferably via one or more incisions in the vaginal wall;

(c) a second tack is tacked through the sling and into a second location on the pubic bone; and (d) any incisions in the vagina are preferably closed, e.g., sewn up.

The above method may be varied in accordance with various preferred embodiments of the invention. In particular, the order of steps may be changed and steps may be combined. In one example, the two tacks may be tacked simultaneously, using a two-headed tacker, as described for example with reference to FIG. 8.

In a preferred embodiment of the invention, the sling comprises a strip of xenograft material. Alternatively or additionally, the sling comprises human cadaver tissue or auto-graft material harvested from the patient. Alternatively or additionally, the sling comprises a synthetic material, for example Dacron mesh. In a preferred embodiment of the invention, the sling is about 1 mm thick, 1-2 cm wide and 5.5 cm long, between the tacked points. It should be appreciated however, that the exact dimensions of the sling may vary responsive to the anatomy of the patient being treated. Possibly, a prior-art sling may be utilized.

In a preferred embodiment of the invention, the sling is reinforced at or near portions thereof through which the tack is inserted and/or portions of the sling engaged by head 44. Alternatively, the sling is not reinforced. Alternatively or additionally, a hole is pre-punched in the sling at or near where the insertion point of the tack. Possibly, the hole is reinforced. The hole may have a shape similar to the cross-section of the shaft or it may be larger or smaller than the cross-section and/or of a different shape. In a preferred embodiment of the invention, one or more slits are formed (and optionally reinforced) in the sling at locations where the tack is to be inserted instead of- or in addition to- punching a hole thereat. Alternatively or additionally, an elliptical or a long rectangular slot may be cut in the strip to accommodate a plurality of tack positions. Alternatively or additionally, a plurality of pre-punched holes and/or pre-cut slits may be provided for that purpose. Excess sling length is optionally removed either prior to or after deployment of the sling. Alternatively or additionally, the sling is formed of two parts, that are glued together to form a sling of a desired length, prior to or after being tacked to the bone.

In a preferred embodiment of the invention, human cadaver based slings do not have pre-provided holes, while synthetic slings do. In some cases, holes are cut just prior to the procedure. Alternatively, the holes are cut in a factory.

In a preferred embodiment of the invention, the sling has a smooth surface. Additionally or alternatively, at least one of the two surfaces of the sling is rough, for example to promote tissue ingrowth. Additionally or alternatively, the sling is coated with tissue growth enhancing or retarding coatings, possibly both, on different parts of the sling. Additionally or alternatively, the sling may have a plurality of barbs, apertures and/or other structures defined thereon to grasp soft tissue, for example the urethra and/or tissue between the urethra and the bone.

In a preferred embodiment of the invention, the sling is pre-loaded on one or both tacks, before the tacking head is inserted into the body. The pre-loading may be performed in a factory or a work shop, where the sling is produced and/or processed. Alternatively, the pre-loading is performed at the operating table, possibly after a desired sling length is determined.

Alternatively, the sling is placed between the tacking head and the bone, inside the body, so that the inserted tack will pass engage the sling before entering the bone. In an exemplary embodiment, one tack is pre-mounted on the sling and is inserted into the bone. The sling is then stretched using a forceps, for example, and a second tack is inserted through the sling into the bone.

In a preferred embodiment of the invention, only two tacks are used, one for each side of the sling. Alternatively, more than two tacks may be used for example, for a wide sling (e.g., two tacks on at least on side of the sling), for an "X" shaped sling or to adjust the length of slings which are not tight enough. In some embodiments, one side is tacked and the other side is sutured or otherwise attached, for example to assist in adjustment. Alternatively, the two ends of the sling may be tacked together at a single point on pubic bone 28, possibly using a single tack, thereby forming a closed loop of the sling. Preferably, that single point is not at the center of the pubic bone.

In a preferred embodiment of the invention, a sling is used to support the bladder neck. Alternatively, such a sling may be provided to support the bladder itself, the urethra and/or other abdominal organs. Bladder support, also known as cystocelle repair, generally requires a wide sling with a plurality of tacks at each end (or wide tacks). Also, such a sling may be used to correct a defect in the abdominal floor from which internal organs protrude, by supporting or suspending such organs. Alternatively or additionally, such a sling may be used for male bladder, urethra or bladder neck suspension. Alternatively or additionally, such a sling may be used for a tongue suspension and/or for suspending other soft tissues in the body.

In a preferred embodiment of the invention, a catheter is inserted into the urethra prior to the procedure, to minimize the risk of accidentally puncturing the urethra. Additionally, such a catheter may be useful when determining a desired sling length.

In a preferred embodiment of the invention, a flap-forming incision (e.g., at location 34) is made in the vagina prior to the first tacking or between the first and second tacking, so that the sling can be brought through the incision, under the flap and into the tissue between the vagina and the urethra. Alternatively, both tacks are tacked (with at least part of the sling still inside the vagina) and then the incision is made in the vagina. In some circumstances, no incision will be made and a significant portion of the sling will remain in the vagina.

Alternatively to making an incision in the vagina, a sub-mucosal tunnel may be formed in the tissue between the vagina and the urethra and the sling and/or a tacker device (described below) passed through the tunnel. In a preferred embodiment of the invention, only a single incision is made and the tunnel is made through that incision, for example using an endoscope. Alternatively, two incisions are made and the tunnel formed between them. As described herein, such tunneling preferably utilizes small incisions in the vagina which are either formed by the tacks passing through the vaginal wall to the bone or prepared in advance for the tacks. The tunneling and/or passing may be performed before the first tacking or between the first tacking and the second tacking. When using a tack where the sling is attached to the tack after the tack is inserted into the bone (described below), such tunneling may even be performed after both tacks are attached to the bone.

In a preferred embodiment of the invention, a small incision and/or hole is made in the vagina for the insertion of each tack. Optionally, tissue which intervenes between the vagina and the pubic bone is moved away from the path of the tack so that the tack compresses only a minimal amount of living tissue (other than the sling) against the pubic bone. Alternatively, the tack may create its own hole in the vaginal wall. As described above, these holes/incisions may be used as an aid to forming a sub-mucosal tunnel which bridges the incisions and is between the vagina and the urethra. In some embodiments of the invention, when a tack is tacked to a bone through the hole, a portion of the sling is pulled, by the tack, out of the vagina and into the hole. In an embodiment where only a single incision is made, both tacks (or only a single one if the tacking is at a single location only) are brought through the same, small, incision.

The tacks are preferably attached to the superior pubis ramus (as shown in the figure). Thus, the sling is angled forward (when the patient is standing). If the bladder neck or the urethra descend suddenly, the neck is then held up by the sling. Alternatively, the tacks may be attached to other parts of the pubic bone, for example its bottom or its front, as the tacks may have a flat head which does not cause contact discomfort. Additionally or alternatively, especially for bladder neck suspension procedures, it may be desirable to tack the tacks higher up on the bone or even on the abdominal fascia.

In a preferred embodiment of the invention, the length of the sling is determined prior to the tacking. Alternatively, after the first tack is inserted, a required sling length may be determined and the sling cut to size. Optionally, any trailing portions of the sling which remain after the tacking are cut off.

Figure 3:
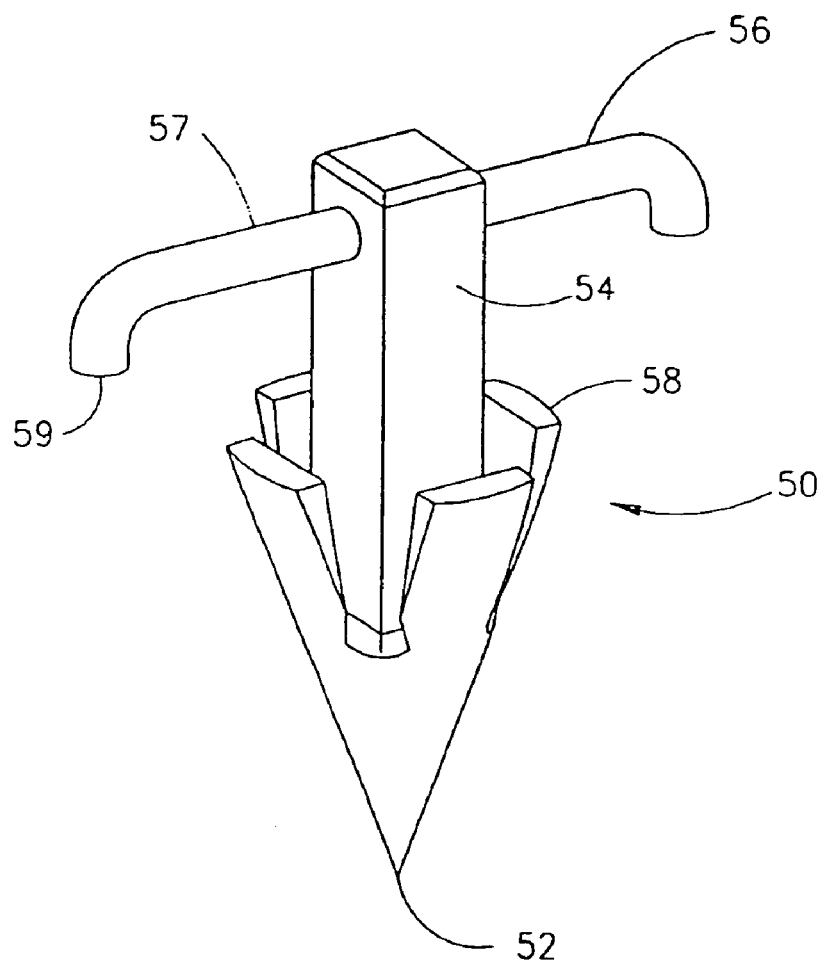
FIG. 3 is a schematic illustration of a tack for attaching a sling to a bone, in accordance with a preferred embodiment of the invention.

FIG. 3 is a schematic illustration of a tack 50 for attaching a sling to a bone, in accordance with a preferred embodiment of the invention. Tack 50 includes a sharp tip 52 for entering the bone, a shaft 54 which grasps the sling and a head 56 for preventing the sling from slipping off the shaft and/or for urging the sling against the bone, to prevent relative movement of the sling and the bone. One or more fins 58 may be provided to improve the bone holding characteristics, however, they do generally interfere with insertion into bone. In some embodiments, fins 58 are flexible. In other embodiments, they are rigid. Alternatively, other constructions for bone piecing and grasping tips, as known in the art, may be used, for example screw-tipped inserts. In a preferred embodiment of the invention, head 56 comprises a pair of extending arms 57. At the tip of each arm (or elsewhere along their length) a protrusion 59 is preferably provided. as will be shown below, sling 40 is preferably urged by protrusions 59 against the bone, however, the entire head may do the urging. Protrusions 59 are preferably flat at their contact point with sling 40. Alternatively, they may be pointed or roughened. Possibly, holes are formed in sling 40 (prior to, during or after insertion), so that at least some of protrusions 59 transfix sling 40 through these holes. Head 56 is preferably flat, however, in some embodiments it may protrude, especially for covering up sharp angles in the head.

In a preferred embodiment of the invention, the arms are perpendicular to the shaft. Alternatively, they may be angled, towards the tip or away from the tip, for example, 10°, 20°, 30° or 45° away from a perpendicular to the shaft. Thus, the tips of the arms can mimic the behavior of protrusions 59. Preferably the arms are super elastic, however, they can also function correctly if they are elastic, plastic or shape memory. The arms may be in the plane of the shaft or outside of the shaft place, possibly not parallel to the shaft plane.

In a preferred embodiment of the invention, a head 56 is wide, for example a circular plate, a sphere or a half-sphere. In some embodiments, the wide head comprises an expanding head, which, once the tack exits the tacker, expands and/or unfolds to have a wide extent. Preferably, the folded/unexpanded head has a diameter similar to that of the shaft, so that the tack is suitable for use in existing anchor insertion devices. In one example, the unfolding head comprises a super-elastic material which is maintained at a deformed (small head diameter) configuration by the tacker. In another example, the expanding head is expanded as a result of pressures applied during the insertion into the bone, for example pressure applied by an anvil portion of the tacker which forces the tack into the bone (described below).

One possible disadvantage of the tack of FIG. 3 is that the diameter of the shaft is smaller than the diameter of the tip. Thus, when the sling is loaded onto the tack, the tip may rip a larger-than-necessary hole in the sling. In some cases, the sling is sufficiently flexible and/or elastic to accommodate the tip.

Figure 4:
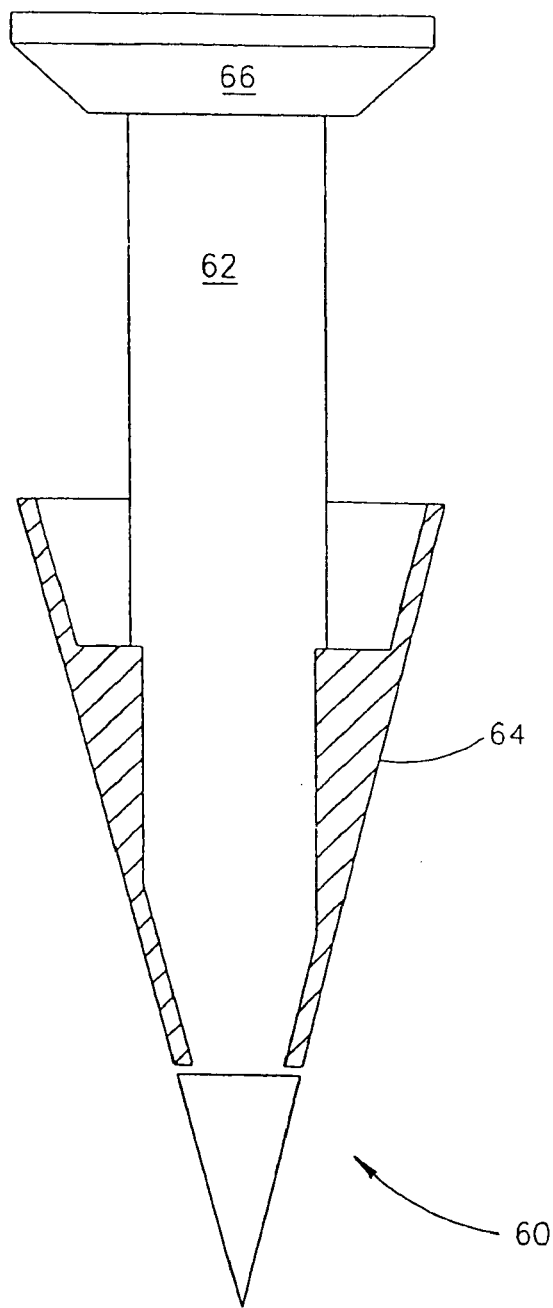
FIG. 4 is a schematic illustration of a two part tack for attaching a sling to a bone, in accordance with a preferred embodiment of the invention.

In a preferred embodiment of the invention, it may be desirable to provide a two part tack, such as tack shown in FIG. 4 as a tack 60, in which a head 66 and a shaft 62 form a first portion, having a small diameter and on which the sling is skewered. Once the sling is skewered by shaft 62, a bone engagement portion 64 is mounted on shaft 62, to form a complete tack 60. The end is result is thus a tack on which a sling, with only a small hole therethrough, is loaded. In some embodiments, head 66 is separate from shaft 62.

Alternatively to using a dedicated tack, a commonly available staple, for example a "U" type staple may also be used to tack the sling to the pubic bone. Thus, the tack may have two or more legs that engage the bone. Possibly however, the quality of the attachment is lower. For example, there may be an increased strain on the sling.

Possibly, the sling is not pierced by the tack at all. Rather the sling is provided between the two or more shafts of the tack (or legs of a staple) and is urged against the bone by the head of the tack and held thereat by friction. Preferably, the portion of the head of the tack that engages the sling is rough or jagged, to better grasp the sling. Additionally or alternatively, a stop is provided on the one or more legs, so that a minimal space is provided between the bone and the head of the tack, for example to prevent undue compression of intervening soft tissue. Additionally or alternatively, the sling may be captured between the shaft and the bone, for example, the shaft has a depression formed in its side and the sling is held between the depression and the portion of the bone which is inside the hole made by the tack. Alternatively or additionally, the sling may be held by holes in the head of the tack (described below).

Additionally or alternatively to using a tack, some preferred embodiments of the invention contemplate other methods of attaching the sling directly to the bone, for example using a quick setting adhesive.

In a preferred embodiment of the invention, once the tack is inserted into the bone, the sling is firmly attached to the bone. In some embodiments of the invention, however, the sling may be fixed to the tack after the tack is attached to the bone. In one example, similar to that of FIG. 4, a thin-headed tack is attached to the bone and only then is the sling loaded onto the tack. Thereafter, the head of the tack is attached and/or expanded, to snugly grasp the sling.

In a preferred embodiment of the invention, a guiding wire or suture is attached to the tack, so that the sling can be guided along the guide wire to the tack, for properly engaging it with the tack head. This wire may then be removed from the tack, as it is does not structurally interconnect the tack and the sling. This embodiment is useful for example if the exact length of the sling is not known in advance. Preferably, the sling has a plurality of holes formed therein, to engage the shaft of the headless tack at various positions along the sling.

Figure 5:
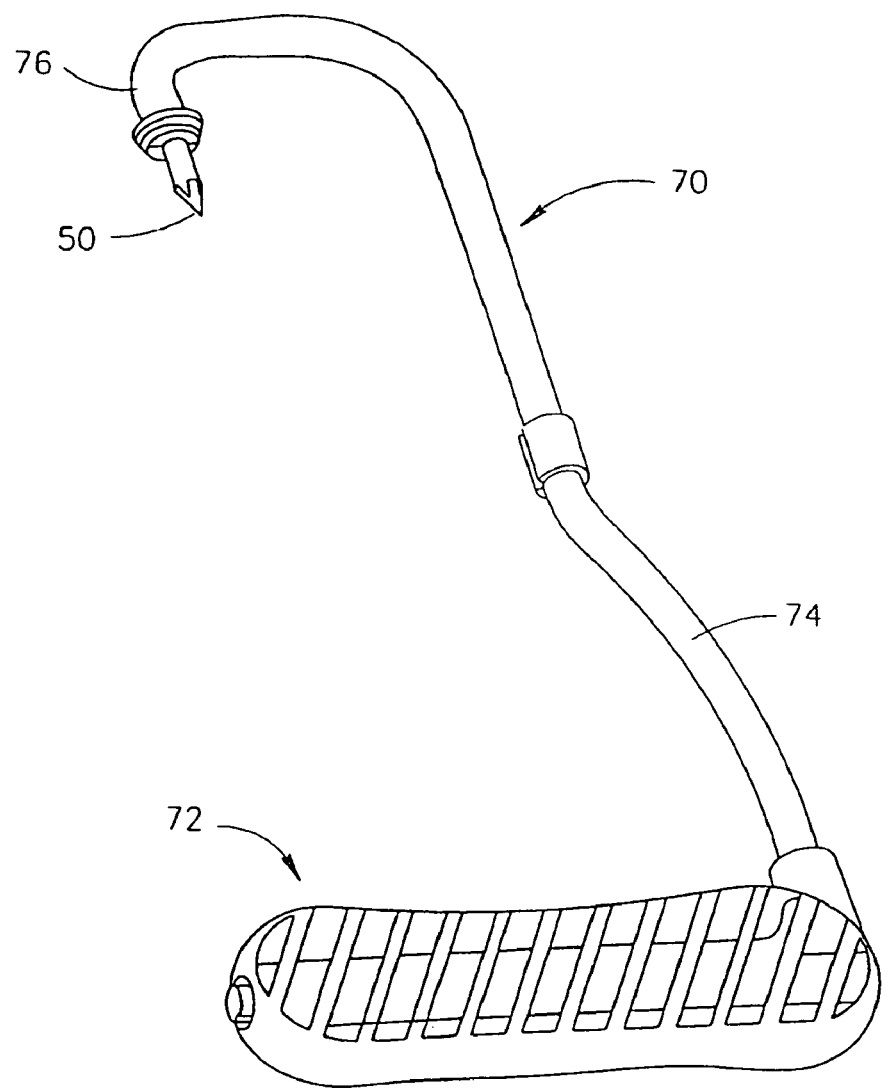
FIG. 5 is a schematic illustration of a tacker for attaching the tack of FIG. 3.

FIG. 5 is a schematic illustration of a tacker 70 for attaching the tack 50 of FIG. 3 to pubic bone 28. Tacker 70 preferably comprises a handle 72, a body 74, which is preferably curved and adapted for use in the vagina and a head 76, which is urged against the pubic bone for inserting a tack. In this embodiment, a tack 50 is mounted at least partially externally to the head. In other embodiments, the tack may be partially or completely recessed inside head 76. Alternatively or additionally, a flexible protecting cover is provided, which cover is pushed back from the tip of the tack to the direction of the head of the tack, by the bone when the tack is pressed against the bone. In a preferred embodiment of the invention, a cartridge of such tacks is attached to head 76 or enclosed in body 74.

In a preferred embodiment of the invention, tack 50 is held onto head 76 by friction, such that, once it is engaged by the bone it can be removed from head 76. Alternatively, a release mechanism (not shown) for preventing the release of the tack may be provided. Alternatively or additionally, such a release mechanism may prevent the tops of fins 58 from exiting the tacker, so that the tack cannot be irrevocably attached to the bone, without activating the mechanism. Preferably, force is applied to the tack by pulling up handle 72, thereby directly pulling back tack 50 into the bone. Alternatively, tacker 70 may include a mechanism for advancing tack 50 into the bone, for example a lever based mechanism or a pneumatic mechanism. In devices with a release or a safety mechanism, the mechanism is preferably released prior to applying the force or during the force application, for example by a lever on handle 72 (not shown).

Figure 6:
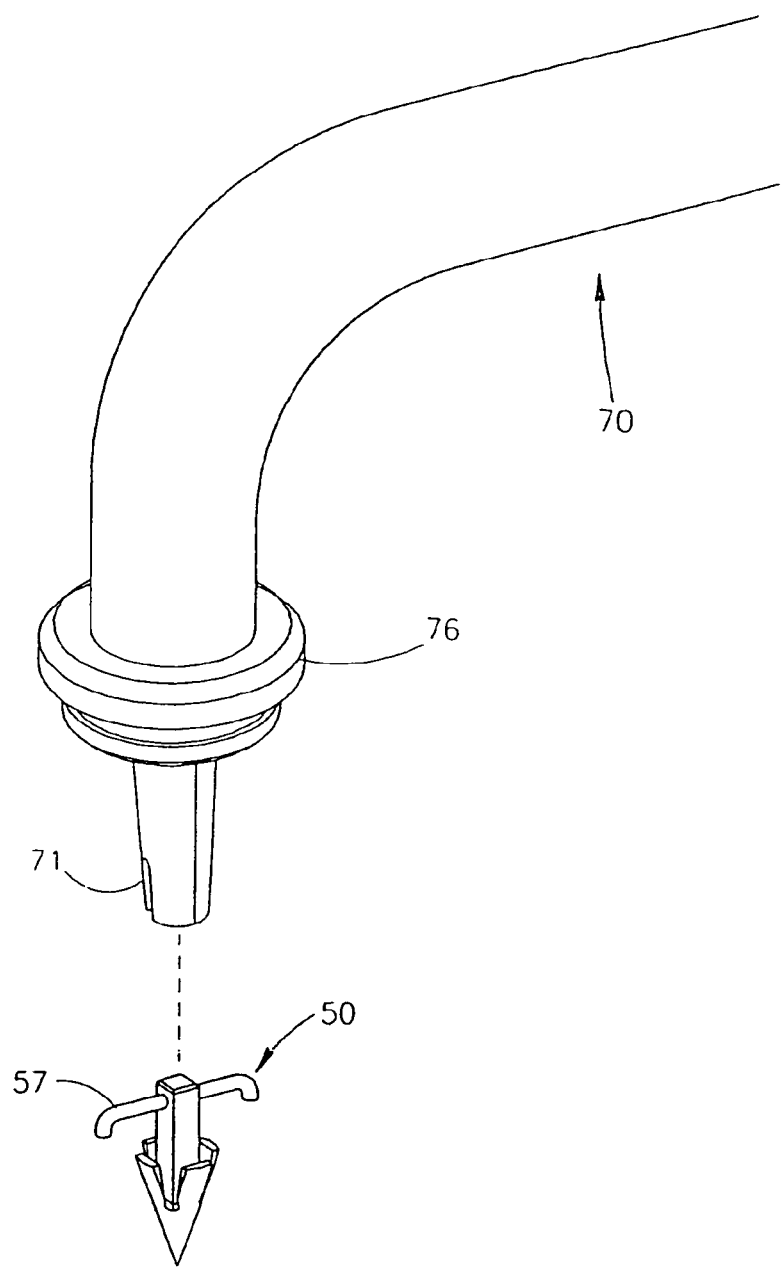
FIG. 6 is a blow-up of a tacking head part of the tacker of FIG. 5.

FIG. 6 is a blow-up of tacking head 76 part of the tacker 70 of FIG. 5. A slot 71 is preferably formed in head 76, to hold arms 57 for the tack configuration shown.

Figure 7:
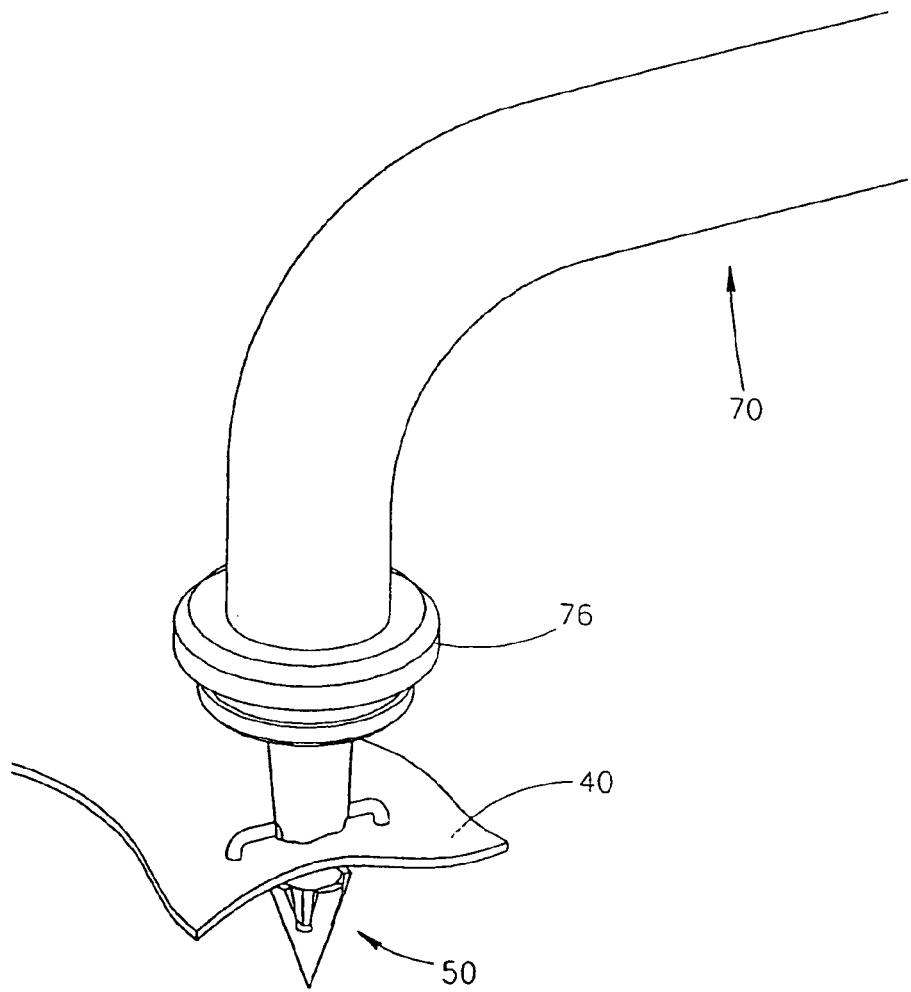
FIG. 7 illustrates a tack which is preloaded on a sling and mounted on a tacker, in accordance with a preferred embodiment of the invention.

FIG. 7 illustrates a tack 50, preloaded on a sling 40 and preloaded on the tacker, in accordance with a preferred embodiment of the invention.

Figure 15A:
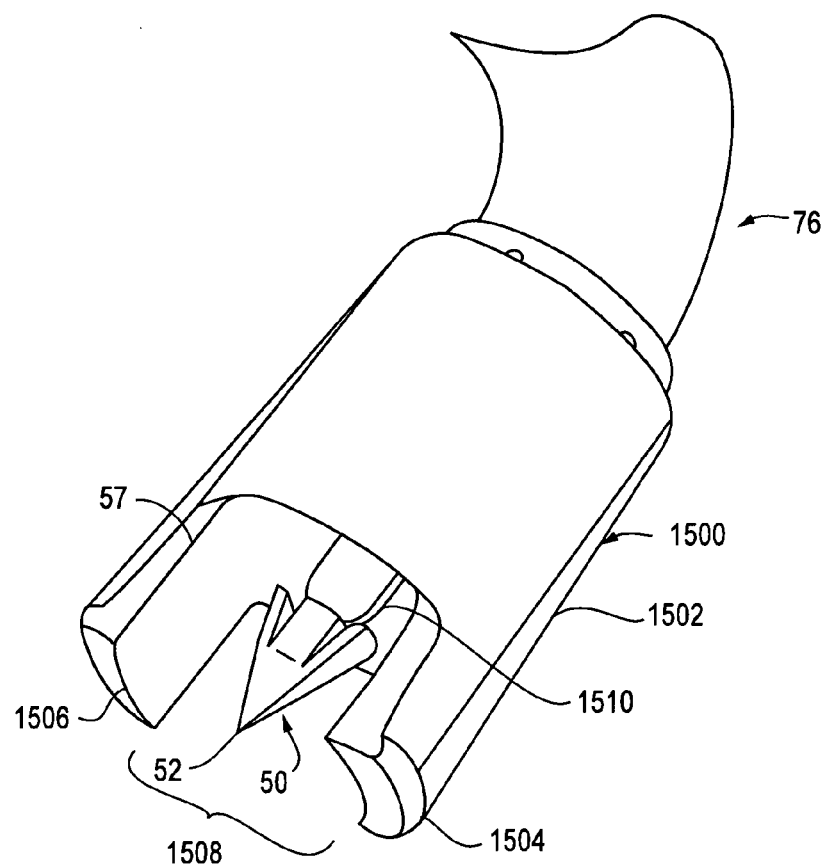
FIG. 15A is a schematic illustration of a tack head, such as shown in FIG. 5, including a slotted shield, in accordance with an exemplary embodiment of the invention.

FIG. 15A is a schematic illustration of a tack head 76, such as shown in FIG. 5, including a slotted shield 1500, in accordance with an exemplary embodiment of the invention. Shield 1500 is provided, for example, to prevent an inadvertent contact between tack 50 and the body. As noted above, such contact can be prevented using a shield, for example a retractable shield, or, as shown here, a flexible shield. In an exemplary embodiment of the invention, when tack head 76 is pressed against a bone with sufficient force, shield 1500 buckles, so that tack 50 can contact the bone.

In an exemplary embodiment of the invention, shield 1500 comprises a body 1502 and two or more extensions 1504 and 1506, that define one or more slots 1508 between them. In an exemplary embodiment of the invention, the slots are provided so that a sling can be mounted on the tack and/or so that such a sling can lay flat, even with the shield in place. The slots may be narrower than, as wide or wider than a sling. Possibly, different shields are provided for different width slings. Alternatively, a single shield with a single slot width or with multiple slots having different widths, is used. Optionally, the shield is adapted for a particular tack size or design. Alternatively, a single shield may be suitable for multiple tack designs and/or sizes.

In an exemplary embodiment of the invention, the slots are straight, as shown. Alternatively, the slots may be wedge shaped, flaring in or flaring out towards the tip of shield 1500. Alternatively or additionally, the slots may be curved or piecewise linear.

Shield 1500 is shown with extension 1504 and 1506 protecting all of head 52 of tack 50, however, they may be shorter, so some of head 52 protrudes. Alternatively or additionally, slots for arms 57 of the tack may also be provided in the shield. As shown, the shield has a diameter greater than the extent of arms 57.

In an exemplary embodiment of the invention, shield 1500 defines a slit or protrusion at a point 1510 at the base of the protrusions, to engage the sling. Possibly, a plurality of such slits or protrusions are defined, for example to support multiple tack sizes. Alternatively, different shields may be used for different tacks.

Figure 15B:
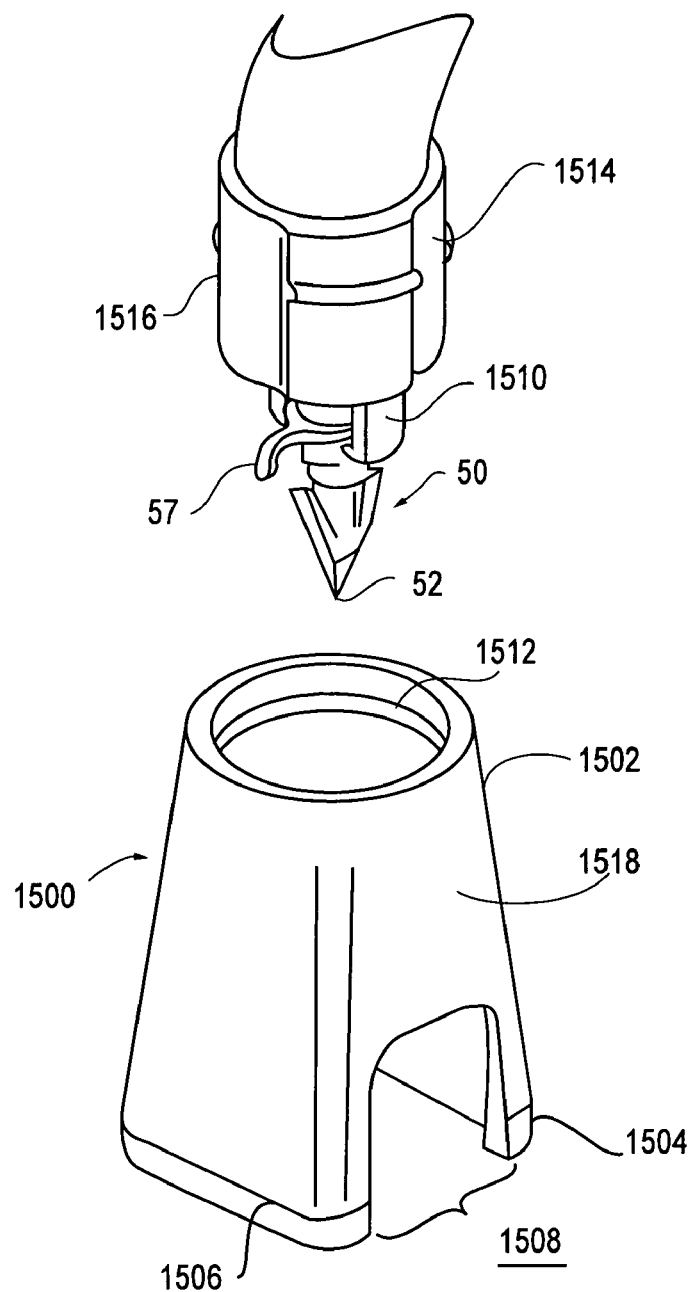
FIG. 15B is an exploded version of FIG. 15A, illustrating an alignment of the shield and the tack head, in accordance with an exemplary embodiment of the invention.

Although a two-slotted shield is shown, in an exemplary embodiment of the invention, only one slot is provided, for one side of the sling to exit. Alternatively, a plurality of slots may be defined, for example for supporting multiple sling orientations. Alternatively or additionally, the shield itself may be designed to maintain one angular position, possibly selected from a set of angular positions FIG. 15B is an exploded version of FIG. 15A, illustrating an alignment of shield 1500 and tack head 76, in accordance with an exemplary embodiment of the invention. In this Fig., shield 1500 is mounted on a shield-engaging portion 1514 of head 76. In an exemplary embodiment of the invention, engaging portion 1514 includes a ring that matches a depression 1512 in shield 1500. Optionally, a directional coupling is defined between head 76 and shield 1500, for example, by defining a planar portion 1516 in engaging portion 1514, that matches a planar portion inside shield 1500 (not shown).

Alternatively or additionally, shield 1500 can be defined to have a non-rotational symmetric cross-section, for example, a rectangle or a triangle. Such a cross-section may also assist tactile sensations inside the body, using the physicians fingers.

In an exemplary embodiment of the invention, shield 1500 is flexible. Alternatively, shield 1500 may be designed to break when sufficient pressure is applied, for example, along an optional fracture line 1518, so that the two extensions 1506 and 1504 fold out of the way. Optionally, the broken pieces remain attached to shield 1500, to prevent leaving foreign objects in the body. In an exemplary embodiment of the invention, shield 1500 comprises a rigid layer (which is broken) and a flexible layer (which holds the pieces together). Alternatively or additionally, shield 1500 may be a retractable shield, for example, using a retraction mechanism (not shown) for retracting the shield when a lever or other control is operated. Alternatively, shield 1500 may slide back along tack head 76, when sufficient pressure is applied to the shield to overcome the engagement of portion 1514. In an alternative type one use shield, the shield cannot be removed from engaging portion 1514, without being damaged, for by portion 1514 and shield 1500 being designed to have a one time interlocking mechanism.

Shield 1500 may be permanently mounted on tack head 76. Alternatively, it may be removable, for example for sterilization. Alternatively, for example as described above, shield 1500 may be a one time use shield.

In an exemplary embodiment of the invention, the sling is mounted on tack 50, after shield 1500 is in place. Alternatively, shield 1500 may be mounted after the sling, for example, by threading the free tip of the sling through the axial openings of shield 1500. Alternatively, shield 1500 may open on its side (for example if line 1518 continues along shield body 1502). Optionally, shield 1500 is then made radially elastic, so that it stays in place. Alternatively, a band may be placed on the shield, to hold it in place. The band may, for example, be removable. Alternatively, the band may comprise a portion of tack head 76 that engages shield 1500.

Figure 16:
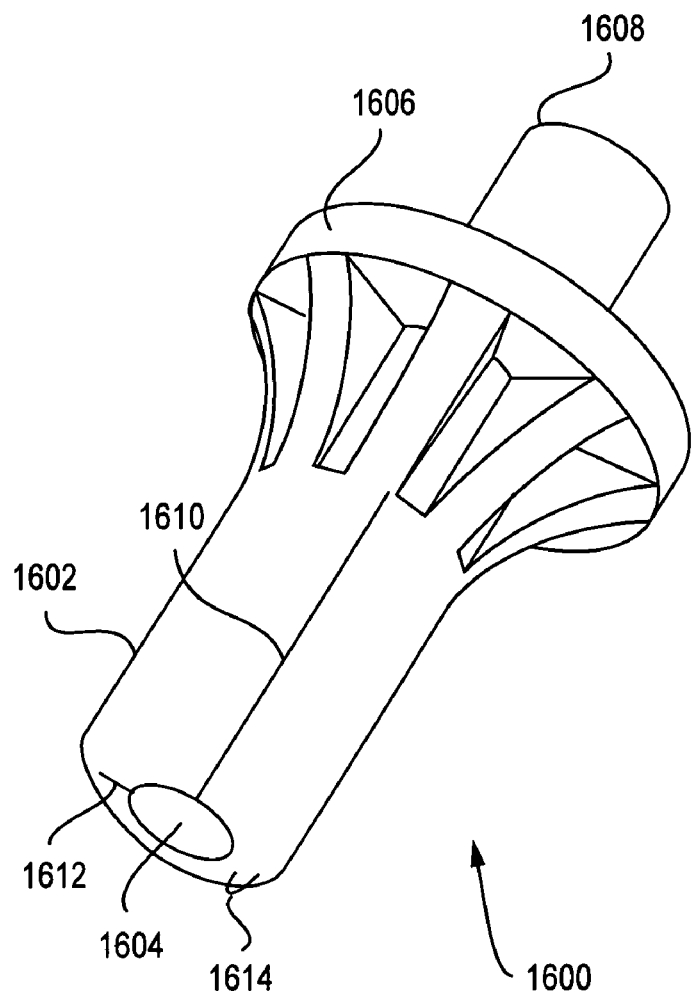
FIG. 16 is a schematic illustration of a sling-mounting implement, in accordance with an exemplary embodiment of the invention.

FIG. 16 is a schematic illustration of a sling-mounting implement 1600, in accordance with an exemplary embodiment of the invention. Implement 1600 may be used to force a sling onto tip 52 of tack 50. The sling may be pre-perforated. Alternatively, the sling may be pierced by tip 52. In an exemplary embodiment of the invention, implement 1600 prevents a person that mounts the sling from inadvertently hurting himself on tip 52.

In an exemplary embodiment of the invention, implement 1600 comprises a body 1602 defining an aperture 1604 at its tip. Aperture 1604 is sized to receive tip 52. Possibly, the cross-section of aperture 1604 also matches tip 52, however, this is not essential. Optionally, implement 1600 includes a handle 1608, for example an extension of body 1602, for example for being held by fingers. Alternatively, another handle type may be provided. Optionally, a finger guard 1606 is provided, so that if aperture 1604 does not engage tip 52 and body 1602 slips by the tip, the tip will not contact fingers holding handle 1608.

In an exemplary embodiment of the invention, aperture 1604 is wide enough so that tip 52 can be retracted after it penetrates the sling. Alternatively, tip 52 is engaged by aperture 1604 and implement 1600 is removed by damaging the implement, for example splitting implement 1600 along an optional split line 1610.

Optionally, implement 1600 is adapted to hold the sling while it is being transfixed on tack 50. In an exemplary embodiment of the invention, a slot 1612 is formed near aperture 1604 and sized to hold the sling. Alternatively or additionally, the tip of body 1602 is made tacky. Alternatively or additionally, sling holder(s) are provided on one or more sides of body 1602.

In an exemplary embodiment of the invention, body 1602 is sized to fit inside shield 1500. Alternatively, body 1602 may be wide enough so that it folds shield 1500. Alternatively or additionally, body 1602 has a cross-section that matches slots 1508 in shield 1500. Alternatively or additionally, finger guard 1606 serves to prevent over-advancement of implement 1600 and the sling over tack 50. Alternatively or additionally, one or more protrusions 1614 are provided at the tip of body 1602 to prevent such an advance, by contacting head 76 or arms 57.

In some embodiments, implement 1600 is designed to be used with non-slotted shields, slotted shields and/or with no shield at all.

In an exemplary alternative embodiment of the invention, aperture 1604 is sized to engage a tip 52 of tack 50. In an exemplary embodiment of the invention, tack 50 is a two part tack, as described herein, and the sling is mounted on the shaft of the tack. Tip 52 is then held by aperture 1604 and pushed, using implement 1600 (a same or different one than used for the sling) onto tack 50.

Figure 8:
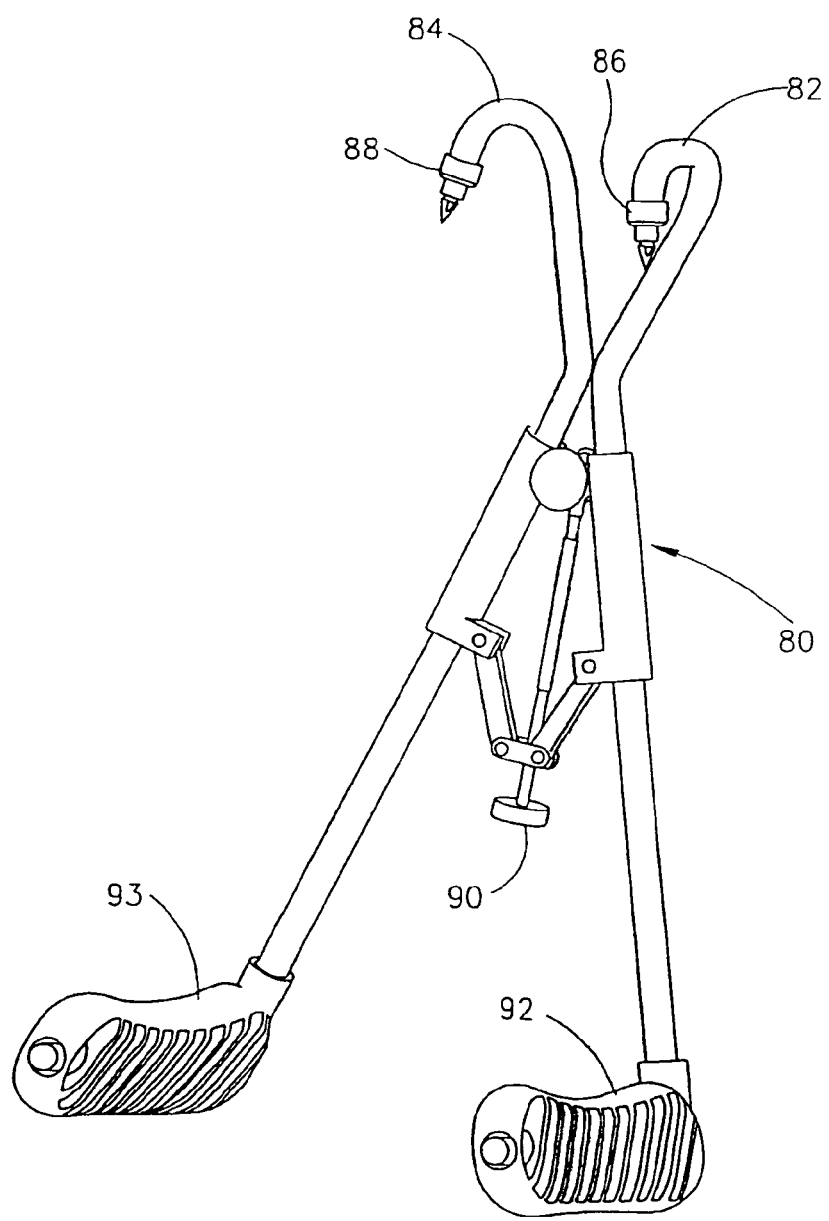
FIG. 8 is a schematic illustration of a two-headed tacker, in accordance with a preferred embodiment of the invention.

FIG. 8 is a schematic illustration of a two-headed tacker 80, in accordance with a preferred embodiment of the invention. Tacker 80 includes two arms, an arm 82 and an arm 84, each with a tacking head, 86 and 88, respectively. In a preferred embodiment of the invention, the distance between the tacking heads may be controlled using a screw 90. Screw 90 may set a maximum and/or minimum distance between the tack heads or it may fix the distance between the tack heads. In one embodiment of the invention, the sling is preloaded on the tacks on the two tacking heads, the two heads are placed in the vagina and the two tacks are simultaneously tacked into the pubic bone. An incision for bringing the sling outside the vagina may be made before or after the tacking. Alternatively, the sling is first brought into the desired area between the vagina and the urethra, possibly using a tunnel and then the sling is loaded (or not) onto the tacks and the tacks are attached to the bone.

In a preferred embodiment of the invention, tacker 80 includes only a single handle 92, which utilizes a single mechanism for advancing both tacks (if such mechanism is provided). Alternatively, the handle includes two separate mechanisms. Alternatively, also a second handle 93 is provided. Each of handles 92 and 93 may have a separate mechanism.

Alternatively to attaching the tacks substantially simultaneously, the tacker may be used to attach the tacks in series, first one and then the other. Optionally, screw 90 includes a sliding mechanism for allowing only one of the two handles to be retracted at a time without also advancing the tack of the other handle. In a preferred embodiment of the invention, setting screw 90 supports fixing the length of the sling outside the body, by setting the distance between the tacking heads (and thus, typically, the tacks).

FIGS. 9A-9D illustrate an alternative tack 100, in accordance with a preferred embodiment of the invention. FIG. 9A is a perspective view of tack 100, showing a tip 102 of a shaft 104, two fins 108 and a head 106, connected to shaft 104 by crimping an extension 112 of shaft 104 to engage a ring portion 110 of head 106. In a preferred embodiment of the invention, head 106 comprises two arms 107, having one or more apertures 105 formed therein. A protrusion 109, preferably wedge shaped, is provided at the end of each arm 107. Optionally, instead of sling 40 being transfixed by shaft 104, sling 40 may be threaded through apertures 105 and/or sutured thereto. Preferably, any knot in the suture is placed between head 106 and the bone.

In a preferred embodiment of the invention, such slings are provided pre-sutured. In a preferred embodiment of the invention, the sutures are in the form of a loop (through which shaft 106 is preferably passed). Such a loop are preferably shortened by knotting, if needed. Alternatively, the sutures are not looped. Such pre-sutured slings may also be used for prior art sling procedures.

FIG. 9B is a top view of tack 100.

FIG. 9C is a side view along the direction of line B-B (FIG. 9B) of tack 100.

FIG. 9D is a cross-section along line B-B (FIG. 9B) illustrating the crimping of extension 112 over ring 110. In a preferred embodiment of the invention, head 106 is thus free to rotate relative to shaft 104, however, this freedom is not essential in all embodiments and may even be explicitly blocked, for example by forming a notch in ring 110.

Figure 10:
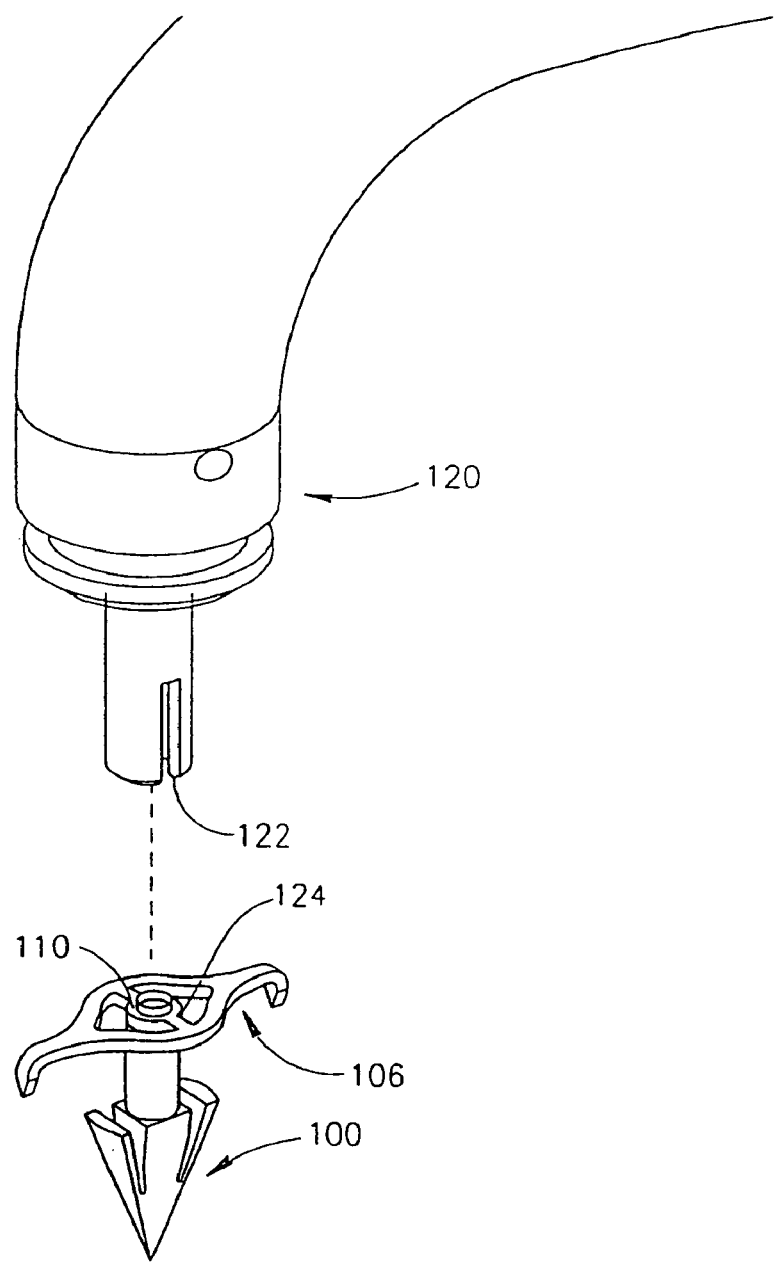
FIG. 10, which corresponds to FIG. 6, illustrates the mounting of the tack of FIGS. 9A-9D on a tacker.

FIG. 10, which corresponds to FIG. 6, illustrates the mounting on a tacker 120 of tack 100. A slot 122 formed in the head of tacker 120 is preferably configured so the head fits in apertures 105, by slot 122 matching a pair of arms 124 that extend between ring 110 and the rest of head 106.

FIGS. 11A-13B illustrate variations in tack designs.

Figure 1:
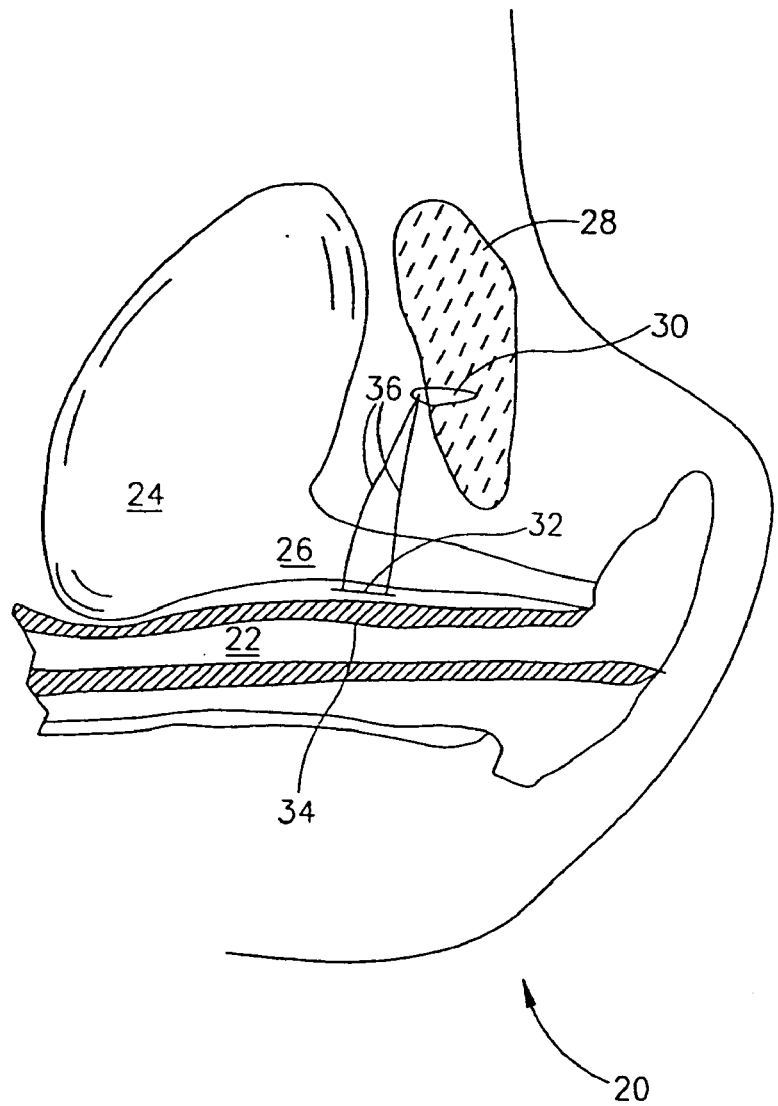
FIG. 1 is a schematic cut-through illustration of a pubic area during a prior art bladder neck support operation.

FIG. 1A is a top view of a tack 130 having four arms 132 (rather than two). Alternatively, other numbers of arms, for example three may be provided. Arms 132 are preferably symmetrically arranged and all of a same length, however, this is not essential and in some embodiments one arm may be shorter or two arms may be closer together than the other arms.

Figure 11A:
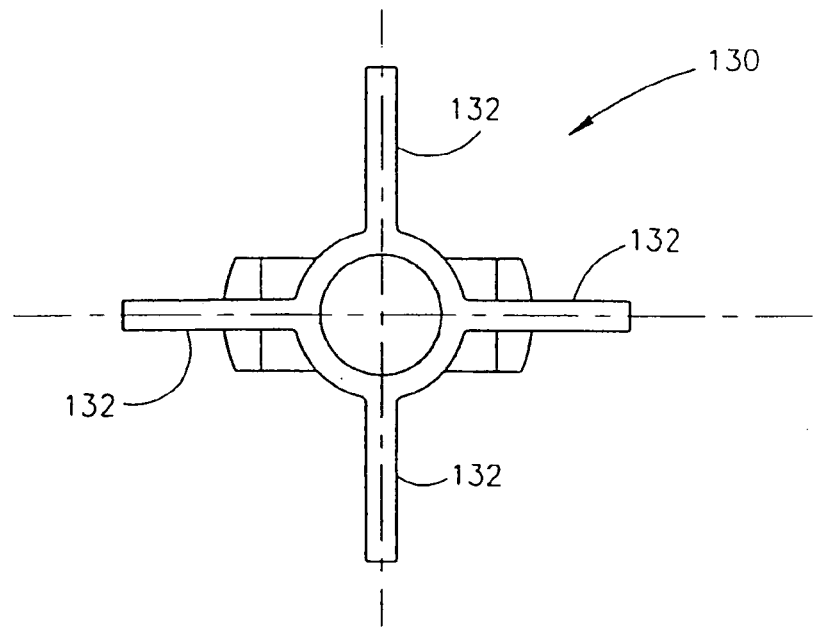
FIGS. 11A-11B illustrate a variation of the tack of FIGS. 9A-9D, in accordance with a preferred embodiment of the invention.
Figure 11B:
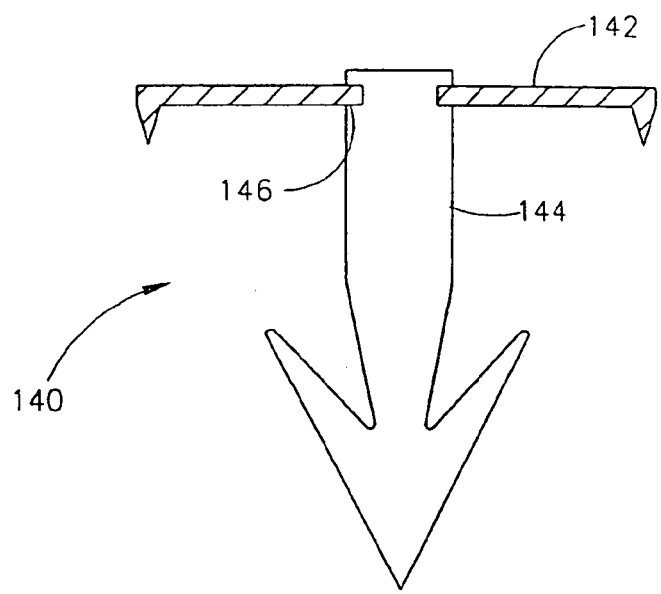

FIG. 11B is a cross-sectional view of a tack 140, corresponding to FIG. 9D and showing an alternative method of attaching a head 142 to a shaft 144, for any type of tack, in which a slot 146 is formed in shaft 144, to receive head 142. An advantage of this method is that an incorrectly placed tack may be corrected by removing the head and advancing the shaft so it is completely enclosed by the bone. In a preferred embodiment of the invention, the head is super-elastic or elastic, so that by applying enough force it can be mounted on the shaft or removed, without permanently distorting it. Alternatively, one time elastic or plastic heads are used, alternatively, a shape-memory material may be used.

Figure 12A:
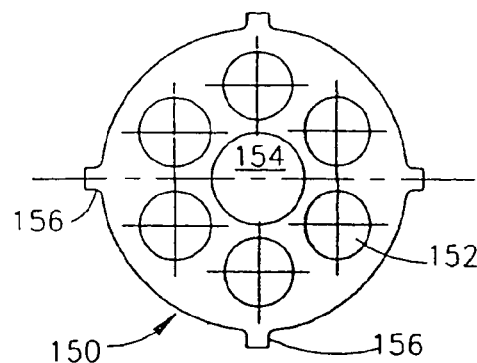
FIGS. 12A-12C illustrate variations of the head of a tack, in accordance with alternative preferred embodiments of the invention.
Figure 12B:
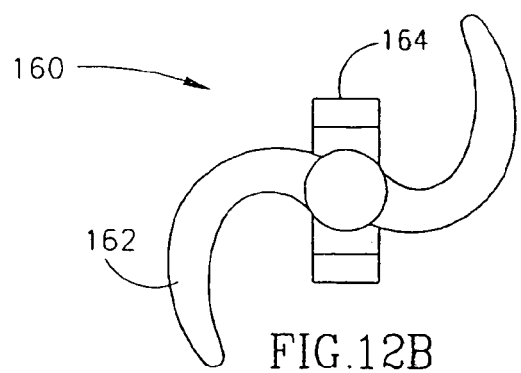
Figure 12C:
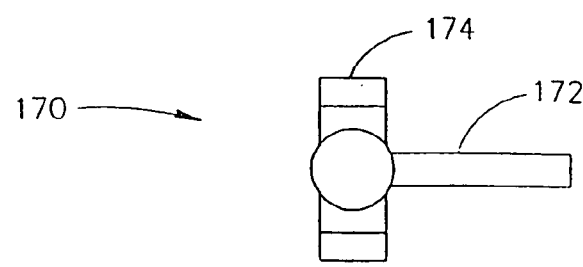

FIGS. 12A-12C illustrates variations of head portions of tacks. FIG. 12A illustrates a head 150 which defines a plurality of apertures 152 therein and has a plurality of protrusions 156 around its perimeter (and also possibly inside the perimeter), which are protrude towards the bone. Central aperture 154 is preferably used to affix head 150 to a shaft of a tack. The apertures may or may not be aligned with the protrusions that most forcefully engage the sling.

FIG. 12B illustrates, in top view, a tack 160, which comprises spiral arms 162, rather than straight arms as described above. An advantage of spiral arms is an increased flexibility of the arms, without compromising their strength. A pair of fins 164 are also shown, for example of the type used in device 100 of FIG. 9.

FIG. 12C illustrates, in top view, a tack 170, which has only a single arm 174. A pair of fins 174 is also shown, perpendicular to the arm. Alternatively, the fins are parallel or oblique to the arm. Alternatively, only one fin 174, preferably opposite arm 172, is used.

Figure 13A:
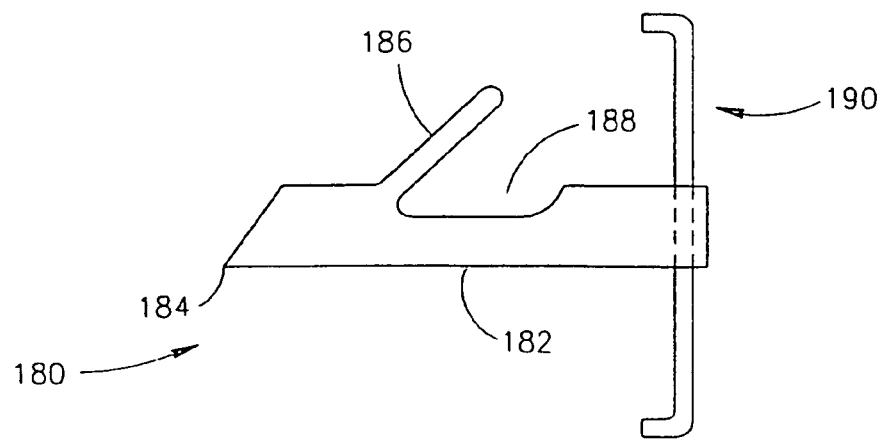
FIGS. 13A and 13B illustrate a recessed fin tack, in accordance with a preferred embodiment of the invention.
Figure 13B:
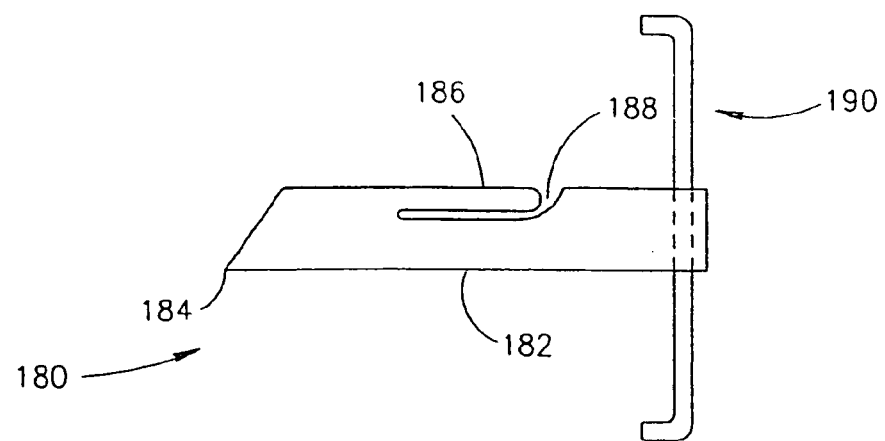

FIGS. 13A and 13B illustrate a recessed fin tack 180, in accordance with a preferred embodiment of the invention. Tack 180 comprises a head 190 attached to a shaft 182 with a tip 184. At least one fin 186, but possibly more than one, extend from shaft 182, as shown in FIG. 13A. In a preferred embodiment of the invention, a recess 188 is formed in shaft 182, to receive fin 182 during insertion into the bone, so fin 186 does not impede the insertion process (FIG. 13B). Preferably, during insertion, the edge of the bone presses fin 182 into recess 188. In a preferred embodiment of the invention, shaft 182 or fin 186 is formed of an elastic, shape-memory or super-elastic material, to assure that fin 186 returns to an extended configuration as shown in FIG. 13A.

Figure 13C:
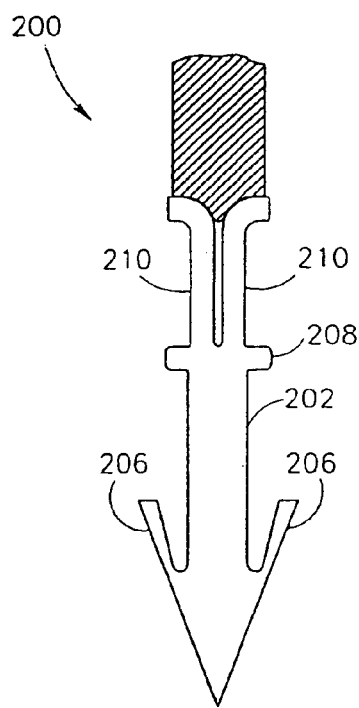
FIGS. 13C and 13D illustrate an expanding head tack, in accordance with a preferred embodiment of the invention.
Figure 13D:
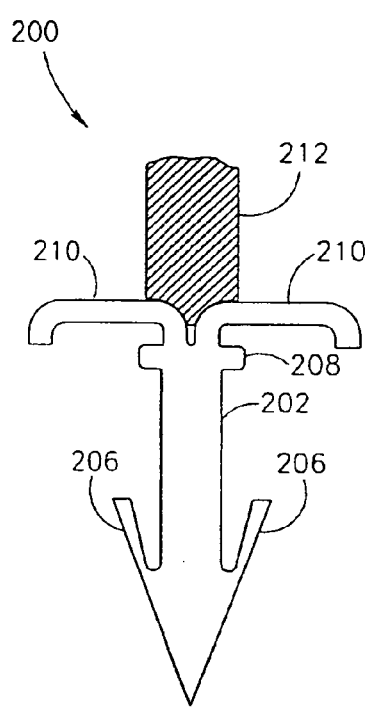

FIGS. 13C and 13D illustrate an expanding head tack 200, in accordance with a preferred embodiment of the invention. Tack 200 comprises a shaft 202, preferably with a plurality of fins 206 at its tips. The head of tack 200 comprises two distortable parts 210. As shown, two or more separate arms are provided, possibly each one with a protrusion as in some of the previous embodiments. Alternatively, an extension of shaft 202 may be split. When the tack is inserted the head may be narrow, as shown in FIG. 13C. When the tack is inserted into a bone, the head is split, for example using a cone shaped element 212, resulting in a tack as shown in FIG. 13D, which can be substantially the same as the tack of FIG. 3. In a preferred embodiment of the invention, an advance-stop 208 is provided, to prevent shaft 202 from advancing too far, especially while portions 210 are being split apart. Such a stop may also be provided in other tack design, for example to provide a minimum distance between the head and the bone. Alternatively, the advance stop is part of the tacking head, for example being in the form of forceps or a "C" shaped element which space the head from the bone and is removed with the tacking head. Possibly, the advance stop is formed of an bio-absorbable material.

In a preferred embodiment of the invention, advance-stop 208 extends away from shaft 202, at least in one transaxial direction, more than portions 210 in their unexpanded configuration. In a preferred embodiment of the invention, a slotted insertion device pushes against advance-stop 208 and an additional internal mandrel is provided to serve as element 212. Thus, portions 210 are distorted plastically. Alternatively, the portions may be formed of a shape-memory material (which can be optionally heated by the tacking head). Alternatively, the portions may be elastic or super-elastic. Preferably, the portions are maintained in their narrow configuration by the slotting head, which, when removed, allow them to snap open to their wide configuration. Alternatively or additionally, a bi-stable or a bimetal-mechanism for configuration change may be used. Such elastic, plastic, shape-memory, super-elastic or other head distorting mechanism may be used with any of the tack-heads described above.

Additional variations in tack design are also contemplated in accordance with preferred embodiments of the invention. For example, the shaft of the tack may have a fixed or a varying profile, which can be, for example, circular, square, rectangular, triangular, fluted and/or spiral. Also, the shaft may be barbed and/or roughened. The tip of the tack may be, for example, smooth, fluted, threaded, spiral, inclined on some sides and flat on the others. Alternatively or additionally, the tip may be oblique, for example as shown in FIG. 13. The fins may be, for example, of a design that is rigid or that folds back towards the shaft during insertion. The arms of the head may be, for example, perpendicular to the shaft or they may be slanted. Possibly, the arm configuration is designed to match an anatomical geometry, such as a bone incline. The fins may be distributed with a rotational symmetry around the shaft axis. Alternatively, they are not. Alternatively or additionally, the fins are all at a same axial position along the shaft. In some embodiments, they are not.

Figure 14:
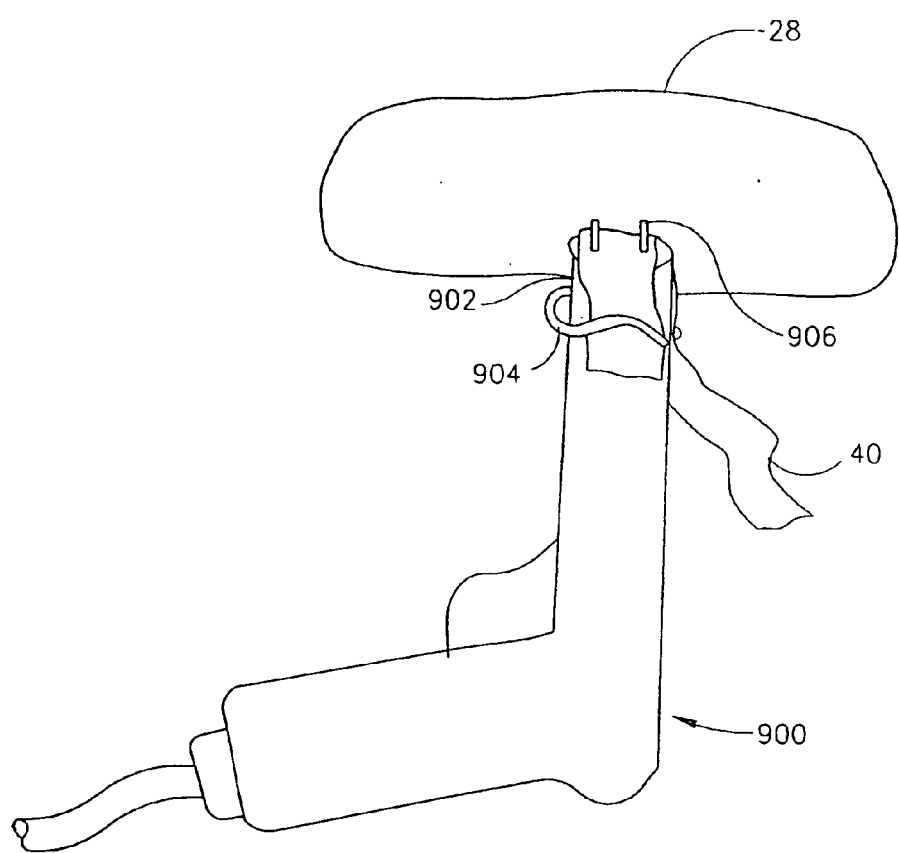
FIG. 14 is a schematic illustration of a sling grasping attachment for a stapler, in accordance with a preferred embodiment of the invention.

FIG. 14 is a schematic illustration of a sling grasping attachment 904 for a stapler 900, in accordance with a preferred embodiment of the invention. As described above, in some cases, even a standard type staple, bone anchor and/or bone screw may be used to attach sling 40 directly to the bone. Such screws and staples usually include a stop for limiting the penetration depth into the bone, which can serve as a tack "head", in accordance with a preferred embodiment of the invention. The portion of a shaft behind the stop, including for example a threadable hole, may be filed off, especially if they are not required for the structural integrity of the bone insert. However, the standardized staplers, anchor insertion devices and other bone attachment apparatus do not appear to provide for a sling that is engaged by the staple. Attachment 904, is an example of an attachment which maintains the sling in a desired position and/or orientation relative to the staple, until the staple is inserted into the bone. In this embodiment, attachment 904 comprises a resilient clip that urges and holds the sling against the body of stapler 900. In other embodiments, the attachment may be mounted over the tacking head, possibly extending the head length. In some cases, for example as shown, a staple 906 may pierce the sling, prior to the act of stapling. In other cases, the tip of the staple is recessed in the stapler and cannot engage the sling. In other embodiments of the invention, other attachments may be provided. In particular, the exact geometry of the attachment may be adapted for a particular stapler model and/or staple type.

In a preferred embodiment of the invention, the above described slings, tacks, shields, tackers and/or sling mounters are provided as a kit. In an exemplary embodiment of the invention, a kit includes one or more slings of possibly varying lengths and two or more tacks. Alternatively or additionally, such a kit includes instructions for using the element(s) in the kit.

Although the above description has focused on female urinary incontinence, a same procedure and apparatus may be used for male incontinence, for example, by attaching the sling to a descending ramous of the pubic bone through an incision in the perineal area.

It will be appreciated that the above described apparatus and methods of incontinence treatment may be varied in many ways. In addition, a multiplicity of various features, both of methods and of devices, have been described. It should be appreciated that different features may be combined in different ways. In particular, not all the features shown above in a particular embodiment are necessary in every similar preferred embodiment of the invention. Further, combinations of the above features are also considered to be within the scope of some preferred embodiments of the invention. It should also be appreciated that many of the embodiments are described only as methods or only as apparatus. The scope of the invention also covers machines for creating the devices. In addition, the scope of the invention includes methods of using, constructing, calibrating and/or maintaining the apparatus described herein. When used in the following claims, the terms "comprises", "comprising", "includes", "including" or the like means "including but not limited to".

What is claimed is:

1. A sling mounting implement adapted for mounting a sling on a tack, comprising:
    a body having a longitudinal axis and proximal and distal ends;
    an aperture defined by said body formed at said distal end said aperture receiving a tip of said tack;
    a radially projecting finger guard extending circumferentially about said longituinal axis, said radially projecting finger guard having structure adapted to protect fingers of a user; and
    a handle located along the longitudinal axis of said body at said proximal end.

2. An implement according to claim 1, wherein said aperture is sized so that the tip of said tack can be retracted after the tip penetrates a sling.

3. An implement according to claim 1, wherein said aperture is sized so that the tip of said tack cannot be removed from said aperture, without damaging the implement.

4. An implement according to claim 1 further comprising a split line located along the longitudinal axis of said body.

5. The implement of claim 4 further comprising a sling received by said slot.

6. The implement of claim 4 wherein said sting mounting iniplement, said tack and said sling are packaged in kit.

7. The implement of claim 1 wherein the distal end of said body includes a tacky substance.

8. The implement of claim 1 further comprising a slot in said body adjacent to said aperture, said slot sized for holding a sling while it is being transfixed on said tack.

* * * * *

UNITED STATES PATENT AND TRADEMARK OFFICE
CERTIFICATE OF CORRECTION

PATENT NO. : 7,226,408 B2 Page 1 of 1
APPLICATION NO. : 10/322891
DATED : June 5, 2007
INVENTOR(S) : Boaz Harari et al.

It is certified that error appears in the above-identified patent and that said Letters Patent is hereby corrected as shown below:

Title Page

Item (75) Title: delete "Boaz Harai" and insert --Boaz Harari--

Column 18, line 24, claim 1, after "end" insert --,--

Signed and Sealed this

Fourteenth Day of August, 2007

JON W. DUDAS
*Director of the United States Patent and Trademark Office*